(12) United States Patent
Carlow et al.

(10) Patent No.: US 6,790,630 B1
(45) Date of Patent: Sep. 14, 2004

(54) **DNA AND PROTEIN FROM *DIROFILARIA IMMITIS***

(75) Inventors: Clotilde K. S. Carlow, Cambridge, MA (US); Francine B. Perler, Brookline, MA (US); XiaQiang Hong, Danvers, MA (US); Jhon Santiago Mejia, Medellin (CO)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/535,679

(22) Filed: Mar. 23, 2000

Related U.S. Application Data

(60) Division of application No. 08/836,236, filed as application No. PCT/US96/04999 on Apr. 9, 1996, now Pat. No. 6,103,484, which is a continuation-in-part of application No. 08/420,976, filed on Apr. 10, 1995, now abandoned.

(51) Int. Cl.[7] ...................... G01N 33/53; G01N 33/543; G01N 33/569; G01N 33/566
(52) U.S. Cl. ................... 435/7.22; 530/350; 530/388.6; 424/266.5; 424/265.1; 424/185.1; 424/184.1; 435/7.22; 435/7.92; 435/69.1; 435/69.3; 536/23.1; 536/23.7
(58) Field of Search ............................... 435/7.22, 7.92, 435/69.1, 69.3; 424/184.1, 185.1, 265.1, 266.1; 536/23.1; 530/350, 388.6

(56) References Cited

U.S. PATENT DOCUMENTS 6,103,484 A * 8/2000 Carlow et al. ............... 435/7.2

OTHER PUBLICATIONS

Kang et al (Journal of Parasitology 1993, vol. 79, 815–828).*
Mejia, "Expression of an Onchocercal Ov33 Homolog in *Dirofilaria immitis*: Potential in Immunodiagnosis of Heartworm Infection," Apr. 10–13, 1994—Woods Hole, Massachusetts.
Mejia, et al., Parasite Immunology, 16:297–303 (1994).
American Heartworm Society, Proceedings Of The Heartworm Symposium (1992), ed. Mark D. Soll. p289, Silent Partners, Inc., Austin, Texas.
Lucius, et al., Journal of Experimental Medicine, 167:1505–1510 (1988a), 168:1199–1204 (1988b).
Lucius, et al., Tropical Medicine and Hygiene, 43:139–145 (1992).
Chandrashekar, et al., Investigation, 88:1460–1466 (1991).
Dissanayake, et al., Molecular and Biochemical Parasitology, 632:143–146 (1993).
Willenbucher, et al., Molecular and Biochemical Parasitology 57:349–352 (1993).
Boto, et al., J. Immunol. 133(2):981–987 (1984).
Parkhouse and Harrison, Parasitology, 99:S5–S19 (1989).
Villanueva and Rodriguez–Perez, Am. J. Trop. Med. Hyg. 48(4):536–541 (1993).
Yamagata, et al., Veterinary Parasitology, 44:223–245 (1992).
Hong, et al., American Society of Tropical Medicine and Hygiene Abstract # 237 (Nov. 16, 1994).
Hong, et al., Parasitology, 112:331–338 (1996).
Entire Poster Presentation Displayed at the American Society of Tropical Medicine And Hygiene Symposium held Nov. 1994.
Hong, et al., Abstract presented at The American Heartworm Society Mar. 31–Apr. 2, 1995.
Hong, et al., A Proceeding of the Heartworm Symposium '95, pp. 141–146 (1996).
Entire Poster Presentation Displayed at the Edna Clark McConnell Foundation Meeting of Apr. 10–Apr. 13, 1994.

* cited by examiner

*Primary Examiner*—Lynette R. F. Smith
*Assistant Examiner*—Padmavathi Baskar
(74) *Attorney, Agent, or Firm*—Harriet M. Strimpel; Gregory D. Williams

(57) ABSTRACT

In accordance with the present invention, a 31–33 kDa glycoprotein of *D. immitis* (DiT33) is provided which represents another member of the family of putative pepsin inhibitors. Other known members include Ov33 (a.k.a. Ov33.3, Oc3.6, OvD 5B), Bm33 and Av33. These filarial molecules possess significant homology to the known pepsin inhibitor (Aspi3) of *A. suum*. Using DiT33 or Ov33, in the form of a recombinant fusion or non-fusion protein, antibody responses to DiT33 may be monitored and used in immunodiagnosis of heartworm infection in mammals. Antibodies reactive with the DiT33 or Ov33 may also be used to detect DiT33 antigen as a means of immunodiagnosis of heartworm infection in mammals.

2 Claims, 11 Drawing Sheets

```
Ov    1 GAATTCCGAA TAATTCCAT 19

20 CAAGAACAACAATGAAAATTCTTTTC.GGTTGTTATTGCTCGC..ATA  67
        ||||||||||||||||||||||||| |||||||||||||||||  |||
      1 CAAGAACAACAATGAAAATTCTTTTCTGTTGTTATTGCTCGGCGATA  50

68 ACAGCATTGGAAGCAGGTGTTAGTAAAAAGGTACAATAAACGTTTTGCTG 117
        |||||||||||||||||| ||||||||||||||||||||||||||||||
     51 ACAGCATTGGAAGCAGGTG.TAGTAAAAAGGTACAATAAACGTTTTGCTG  99

118 GATTTAATGTTGCCGGAATTGGTGG..AATGCTGGATGTGTCGTTGTGGGA 166
        ||||||||||||||||||||||||   ||||||||||||||||||| |||
    100 GATTTAATGTTGCCGGAATTGGTGGAAATGCTGGATGTGTCGTTGT.GGA 148

167 TTTTAAT.AACTGTT 180
        |||  ||| |||||
    149 ...TAATAAACTGTT 160
```

FIG. 5

```
CCCAAGTTTGAGAATTACTTGGATTATACAAAATCGAGAATATTTCAACAAAATAAAACT    60

ATGAAAATTCTTTTCTGTTTCGTATTGCTTGCGATAGCAGCATTGCGAGCAAGCGTCATA   120
 M  K  I  L  F  C  F  V  L  L  A  I  A  A  L  R  A  S  V  I    20

AATCGACACAACAAACGTTTTGCCGGATTCAGTGTGTTGCTGGAATTGGTGGAACTGCCGGA  180
 N  R  H  N  K  R  F  A  G  F  S  V  A  G  I  G  G  T  A  G    40

TGTGTTGTTGTTGATAATAAACTTTTTGCGAACAGCTTCTATCTTCGTGATCTAACAACC   240
 C  V  V  V  D  N  K  L  F  A  N  S  F  Y  L  R  D  L  T  T    60

GAAGAGCAAAGAGAACTGCACAATATGTTGAAGATTCAAATCAATACAAAGAAGAAGTA    300
 E  E  Q  R  E  L  A  Q  Y  V  E  D  S  N  Q  Y  K  E  E  V    80

AAGACATCATTGGAAGAAAGACGTAAAGGATGGCAATTAGCACGACATGGTGAGAAGGAT   360
 K  T  S  L  E  E  R  R  K  G  W  Q  L  A  R  H  G  E  K  D   100

GCTAAAGTTTTATCATCATTAGCAGAAAAGAAATTCCCAAAACCACCAAAAAACCATCA   420
 A  K  V  L  S  S  L  A  E  K  K  F  P  K  P  P  K  K  P  S   120
```

FIG.6A

```
TTCTGCTCAGCTGGTGATACGACACAATACTATTTGATGGTTGTATGGTTCAGAATAAT    480
 F  C  S  A  G  D  T  T  Q  Y  Y  F  D  G  C  M  V  Q  N  N    140

AAAATATATGTGGGACGAATGTATCGTGATTTAACATCCGATGAAATAAATCAACTG      540
 K  I  Y  V  G  R  M  Y  V  R  D  L  T  S  D  E  I  N  Q  L    160

AAAACATTTGATGCTAAAATGACAGCATATCAGAAATATTTGTCATCGTCCATTCAACAG   600
 K  T  F  D  A  K  M  T  A  Y  Q  K  Y  L  S  S  S  I  Q  Q    180

CAAGTTGATAGCTTTATTGGTGATAAATCAAATCTATTCAATTTATTCACTGATACACGT   660
 Q  V  D  S  L  F  G  D  K  S  N  L  F  N  L  F  T  D  T  R    200

CATGAAACATCATCACAACCATCCGATGCTACAACAATCTCGACAACAACTCAAGCTCCA   720
 H  E  T  S  S  Q  P  S  D  A  T  T  I  S  T  T  T  Q  A  P    220

GTTGAACCACCCGAAACACCACCATTTCTGTATTGCAATTTATTAAACAAAAAAAAAAAA   780
 V  E  P  P  E  T  P  H  F  C  I  A  I  Y                      235

AAAAG                                                           785
```

FIG. 6B

| | | | | | | |
|---|---|---|---|---|---|---|
| DiT33  | MKILFCFVLL | AIAALRASVI | NRHNKRFAGF | SVAGIGGTAG | CVVVDNKLFA | 50 |
| Ov33   | .....LL..  | ..T.E.G.V  | K.Y....... | N......... | .......... | 50 |
| Av33   | ....S.LL.C | T.TV.EGN.M | .......... | N......... | .......... | 50 |
| Bm33   | ..T...LL.F | ..V.E.GIV  | K.Y....... | N......... | .......... | 50 |
| Aspi3  | ---------- | ---------- | --------Q. | LFSMST.PFI | .T.K..QV.V | 22 |
| DiT33  | NSFYLRDLTT | EE---QRELA | QYVEDSNQYK | EEVKTSLEER | RKGWQLARHG | 97 |
| Ov33   | ...F..E... | ..------   | .......I.. | ......E... | .......D.. | 97 |
| Av33   | .G.F..E..A | ..------   | .......E.K | ...L.V.... | ......I..QS | 97 |
| Bm33   | YGLP..E..A | ..------   | ...K..S R. | QE..K.. .DLM | .......... | 97 |
| Aspi3  | ANLPWTM.EG | DDIQVGK.F. | AR....CTNV. | HDMA------ | ---------- | 56 |
| DiT33  | EKDAKVLSSL | AEKKFPKPPK | KPSFCSAGDT | TQYYFDGCMV | QNNKIYVGRM | 147 |
| Ov33   | KE.S....A. | ....L..... | .......... | .......... | ..D......A | 147 |
| Av33   | ..G..I..TI | T..NL..... | .......T.A | .......... | ......F..QS | 147 |
| Bm33   | ..GS.I.... | ......N... | .......T.A | .......... | ..........T | 147 |
| Aspi3  | ---------- | ----.TCT.  | P.P..GPQ.M | KMFN.V..S. | LG..LFIDQK | 91 |

FIG. 7A

```
         ******
DiT33    YVRDLTSDEI NQLKTFDAKM TAYQKYLSSS IQQQVDSLFG DKSNLFNLFT    197
Ov33     .......P..V T.........  .........  ..K......  E........A   197
Av33     .....A..A KE...S..V..  .........  ....MN...  ...T...L...   197
Bm33     L.....IPE.V KE........  .........  .....M.N..  ...T...S...  197
Aspi3    ......AKDH AEVQ..RE.I A.FEE----  ---------  ---------    116

DiT33    DTRHETSSQP S-DATTISTT TQAPVEPPET PHFCIAIY                234
Ov33     ...T.AT..A .D...AGA..  .......A.P  ....V...               235
Av33     N.HL.ST..A .-E.....P..  ..T..A...  .S..VP..               234
Bm33     E.YL...P.T G-E..-V...  ..V..A...  .S......               233
Aspi3    ----QQEN.. PSSGMPHGAV PAGGLS..PP .S..TVQ-                149
```

FIG. 7B

DNA AND PROTEIN FROM *DIROFILARIA IMMITIS*

This is a Divisional Application of U.S. application Ser. No. 08/836,236 filed Apr. 29, 1997, now U.S. Pat. No. 6,103,484, which was the National Stage Application of PCT/US96/04999 filed Apr. 9, 1996, which is a Continuation-In-Part of U.S. application Ser. No. 08/420,976, filed Apr. 10, 1995, now abandoned.

BACKGROUND OF THE INVENTION

*Dirofilaria immitis* is the causative agent of the heartworm disease in dogs, cats and wild canids, and is occasionally transmitted to humans resulting in pulmonary dirofilariasis. Prevalence values as high as 40% are found in some areas of the United States (Falls & Platt, *American Journal of Veterinary Research*, 43:738–739 (1982), and routine diagnostic screening has been recommended in an effort to control and manage the disease (American Heartworm Society, *Proceedings of the Heartworm Symposium*, 1992 (ed. Soll, M. D.), pages 289–294).

Traditionally, diagnosis relied exclusively on the detection of microfilariae in the blood. However, this method proved inadequate since a significant percentage of animals harbor occult infection, in which adult worms are present but there are not circulating microfilariae. More recently, commercial antigen test kits have become available which detect circulating female worm antigens. While these tests are highly specific, they have been shown to lack sensitivity for pre-patent or non-patent infections (Courtney, et al., *Proceedings of the Heartworm Symposium*, 1986 (ed. Otto, G. F.), pages 77–82; Dzimianski & McCall, *Proceedings of the Heartworm Symposium*, 1986 (ed. Otto, G. F.), pages 83–86; Wong & Fuller, *Proceedings of the Heartworm Symposium*, 1986 (ed. Otto, G. F.), pages 99–105; Courtney *Journal of the American Animal Hospital Association*, 24:27–32 (1988); Wong & Thomford, *Journal of the American Animal Hospital Association*, 27:33–38 (1991)).

Similar problems are encountered in diagnosis and management of the related filarial parasites of humans which are responsible for lymphatic filariasis (*Brugia malayi, B. timori* and *Wuchereria bancrofti*) and onchocerciasis (*Onchocerca volvulus*). However, a number of antigens from these parasites have now been identified which may be useful in diagnosis. Ov33-3 (Ov33) from *O. volvulus*, was one of the first filarial antigens reported to possess immunodiagnostic potential (Lucius, et al., *Journal of Experimental Medicine*, 167:1505–1510 (1988a)). The antigen was subsequently cloned by a number of investigators (Ov33.3 (Lucius, et al., *Journal of Experimental Medicine*, 168:1199–1204 (1988b)); Oc3.6 (Chandrashekar, et al., *Journal of Clinical Investigation*, 88:1460–1466 (1991)); OvD5B (Celine Nkenfou, Thesis, "Molecular Cloning of Genes Coding Antigens Specific For *Onchocerca volvulus*: Evaluation of Expressed Proteins For Use In The Diagnosis Of Onchocerciasis" University of Cameroon (1993)) and additional studies using recombinant antigen corroborated the earlier findings (Chandrashekar, et al., supra, Lucius, et al., *Tropical Medicine and Parasitology*, 43:139–145 (1992); Nkenfou, supra.) Perhaps surprisingly, homologs of this antigen have been found in other filarial parasites including *B. malayi* (Bm33) (Dissanayake, et al., *Molecular and Biochemical Parasitology*, 62:143–146 (1993)) and *Acanthocheilonema viteae* (Av33) (Willenbucher, et al., *Molecular and Biochemical Parasitology*, 57:349–351 (1993)). Interestingly, Bm33 was also shown to possess diagnostic potential for lymphatic filariasis (Dissanayake, et al., supra).

More recently, we described a 33 kDa antigen (DiT33) from *D. immitis* which reacts with sera generated against recombinant OvD5B, indicating the presence of a homolog in heartworm also (Mejia, et al., *Parasite Immunology*, 16:297–303 (1994)). A similar molecule exists in the intestinal nematode *Ascaris suum* since Ov33, Av33 (Willenbucher, et al., supra) and Bm33 (Dissanayake, et al., supra) share significant homology to an aspartyl protease inhibitor of *A. suum* Aspi3 (Martzen, et al., *Biochemistry*, 29:7366–7372 (1990)). However, the *A. suum* protein has not been assessed for diagnostic potential.

The inability to detect pre-patent infection with *D. immitis* limits surveillance and control activities, and results in delays in the evaluation of new therapies. Therefore a procedure for detecting early infection would be a useful tool in the management of heartworm infection.

SUMMARY OF THE INVENTION

In accordance with the present invention, an antigen from *D. immitis*, DiT33, has been identified, purified and cloned. DiT33 as well as the antibody responses generated by DiT33 may be used in early (approximately 11 weeks post-infection) immunodiagnosis of heartworm infection in mammals, and in particular in cats and dogs. DiT33 prepared in accordance with the present invention is substantially free of other antigen determinants from *D. immitis*.

More specifically, purification and expression of DiT33, which we have determined to be an *Onchocerca volvulus* Ov33 homolog was demonstrated in *Dirofilaria immitis*. Rabbit antiserum raised against a recombinant fusion protein of *O. volvulus*, MBP/OvD 5B (Ov33), was found to react with a 31–33 kDa glycoprotein (DiT33) of adult worms of *D. immitis*. An antibody response to MBP/OvD 5B was observed in dogs, as early as 11 weeks post infection with infective larvae of *D. immitis*, and in dogs with occult infection. Cats both experimentally and naturally infected with *D. immitis* also reacted strongly with the recombinant antigen. In contrast, sera from dogs receiving chemically-abbreviated infection or from animals harboring a variety of other helminths failed to react.

Isolation and characterization of a complete cDNA encoding DiT33 from *D. immitis* is also described. DiT33 is expressed in *Escherichia coli* as a fusion with matose-binding protein (MBP). Using this fusion system, serological analysis was performed using a panel of clinically defined dog sera, including samples from dogs infected with other common parasites which present a challenge for heartworm diagnosis. The results of this study confirmed that DiT33 is a member of the putative aspartyl protease (pepsin) inhibitor family, and indicate that DiT33 is a prime candidate as an early marker for *D. immitis* infection.

OvD 5B of dogs harboring *D. immitis* (□), *Dipetalonema reconditum* (Δ) or intestinal worms (o) was examined by ELISA.

Figure 4:
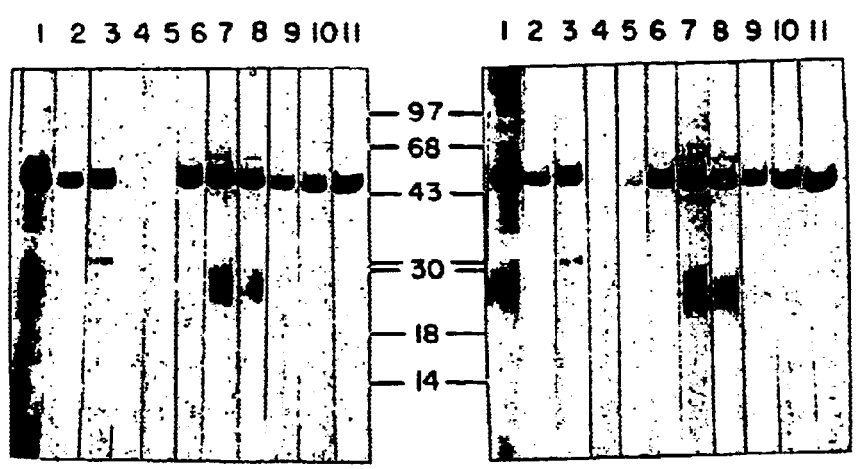
Figure 8A:
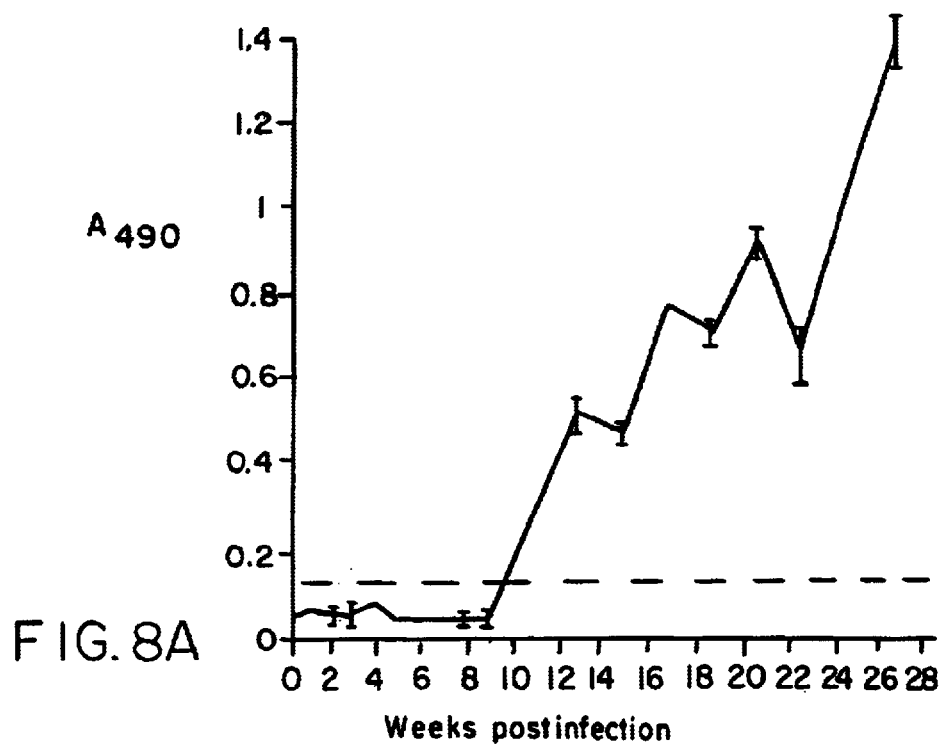
Figure 8B:
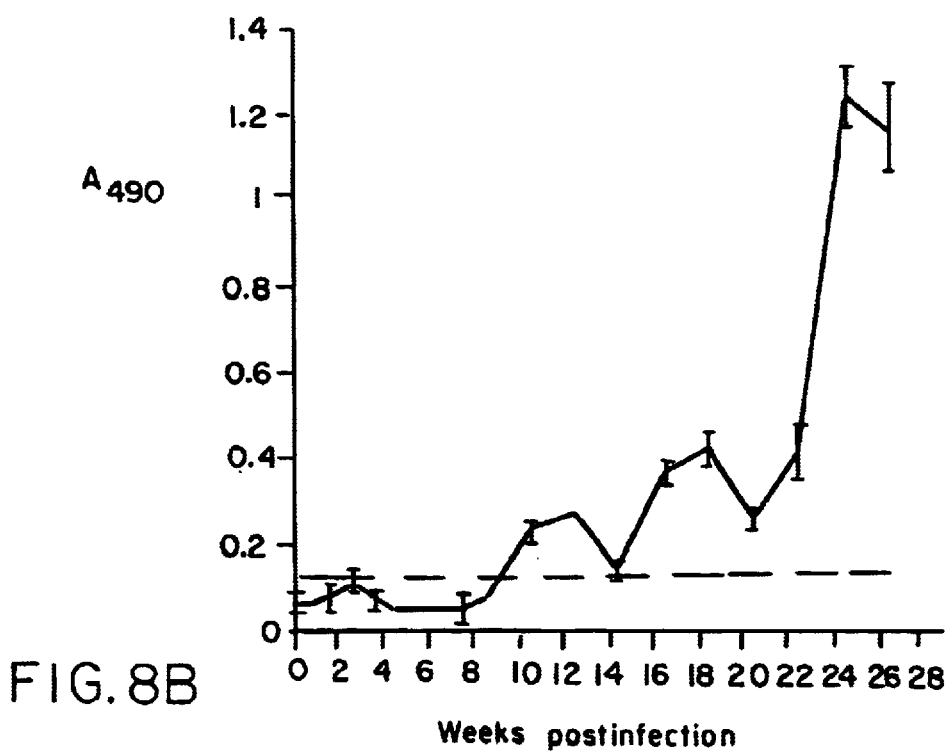
Figure 8C:
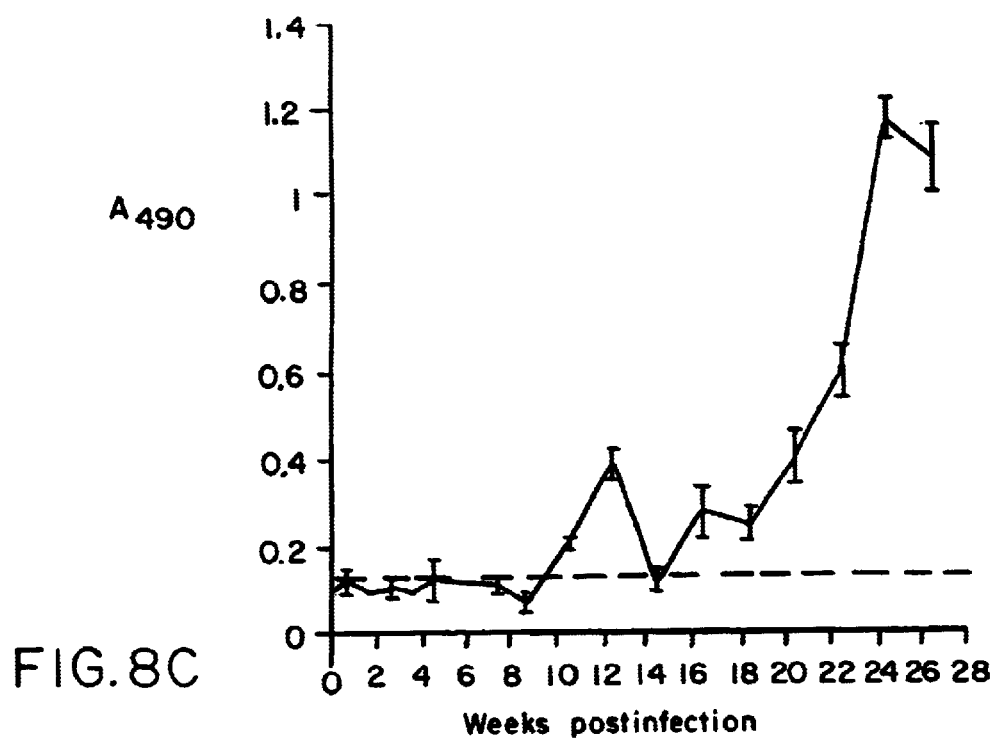
Figure 8D:
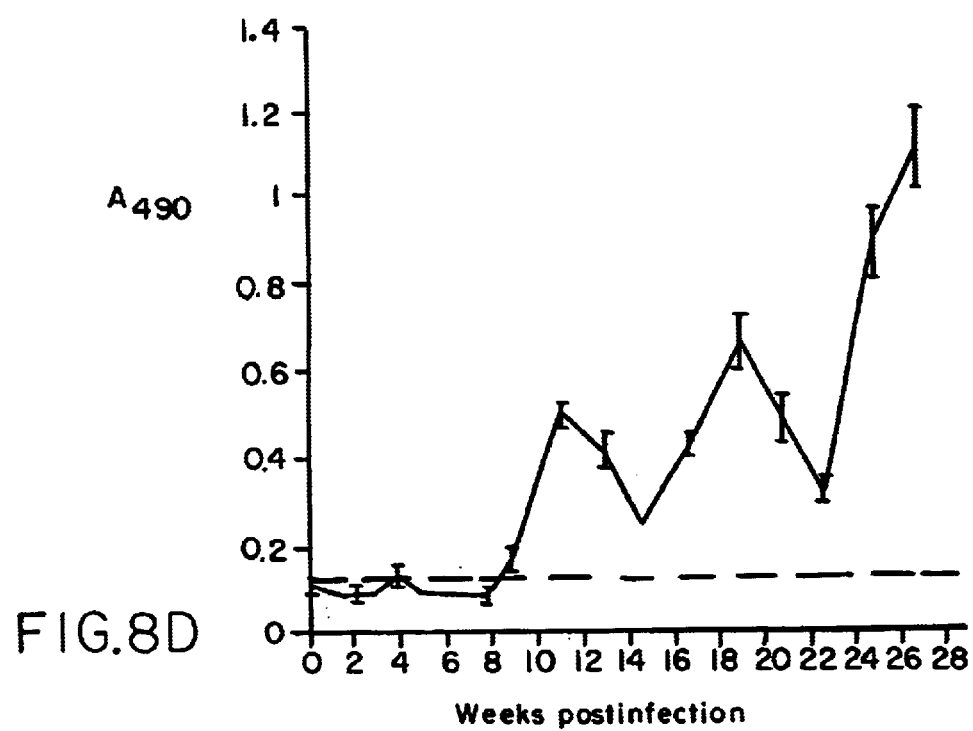

FIG. 4 illustrates the lectinblot analysis of affinity purified Ov33 from *O. volvulus* (a) and DiT33 from *D. immitis* (b) adult worms. Individual lanes illustrate the reactivity of these molecules (see arrows) with the following lectins: Con-A (lane 1), ECL (lane 2), jacalin (lane 3), LEA (lane 4), PNA (lane 5), PHA-E (lane 6), $RCA_{120}$ (lane 7), SBA (lane 8), SJA (lane 9), $VvB_4$ (lane 10) and WGA (lane 11). The 45 and 25 kDa bands represent the heavy and light chains of rabbit immunoglobulins.

FIG. 5 is the preliminary sequence of OvD 5B (SEQ ID NO:1) with primer NEB 1237 compared to the sequence (SEQ ID NO:2) of Ov33-3 (Note that the OvD 5B sequence is from a single sequencing run and probably contains sequencing errors). The top line is the OvD 5B sequence and the bottom line is the Ov33-3 sequence. Vertical bars indicate identity between the sequences, periods represent introduced gaps in the sequence. The OvD 5B sequence begins with an EcoRI site (GAATTC) which is probably from the linker used to construct this library.

FIG. 6 is the nucleotide sequence (SEQ ID NO:3) of the DiT33 cDNA and the deduced amino acid (SEQ ID NO:4) sequence. Amino acids are designed by one-letter symbols. The stop codon is indicated by * * * . The partial spliced leader sequence is underlined.

FIG. 7 shows the alignment of DiT33 (SEQ ID NO:5) with other members of the putative pepsin inhibitor family. Database accession numbers for the previously sequences members are: Ov33, JL0075 (PIR) (SEQ ID NO:6); Av33, S23229 (PIR) (SEQ ID NO:7); Bm33, L11011 (GenBank) (SEQ ID NO:8); Aspi3, A35701 (PIR) (SEQ ID NO:9). Alignment begins at the putative initiating methionines. Amino acid residues identical to those of DiT33 are prepresented by dots. Gaps are represented by dashed lines. The conserved cysteine residues and the six amino acids of the putative active site are indicated by asterisks. The alignment was performed using the PILEUP program of the GCG software package.

FIG. 8A through FIG. 8D illustrate the IgG responses to MBP/DiT33 measured by ELISA in four individual dogs (8A–8D) following an experimental infection of *D. immitis*. Dogs which were micofilaremic on week 27 are indicated by an asterisk. Sera were diluted 1:100 and tested in triplicate. Values represent mean±one standard deviation. Dashed lines represent the cut-off for positive signals.

DETAILED DESCRIPTION OF THE INVENTION

In accordance with the present invention, a 31–33 kDa glycoprotein in *D. immitis* (DiT33) is provided which represents a member of the putative pepsin inhibitor family. Other members include the filarial molecules Ov33 (Ov33.3, Oc3.6, OvD 5B), Bm33 and Av33. These filarial proteins share significant homology to a known pepsin inhibitor (Aspi3) from the intestinal nemade *A. suum*. Using DiT33 and/or OvD 5B, or a recombinant fusion (or non-fusion) protein of *O. volvulus*, OvD 5B or DiT33, antibody responses to DiT33 may be monitored and used in the immunodiagnosis of heartworm infection in mammals. Alternatively, DiT33 or OvD 5B may be used to develop a diagnostic test for measuring circulating antigen in mammals, and in particular dogs and cats. These diagnostic approaches overcome one of the major shortcomings of commercially available antigen tests, namely the lack of sensitivity for pre-patent or non-patent infections by *D. immitis*.

There are several important attributes that are required of an antigen to be useful as marker for heartworm infection. The antigen should be species specific, expressed by immature worms but not infective larvae, and be sufficiently immunogenic to be detected directly in an antigen test or indirectly in an antibody test. The antigen(s) which are used in the latest generation of commercially available antigen detection assays meet all the above criteria, with one exception. These antigens are only produced by mature, fecund females and consequently the tests do not score positive in an infected dog until a considerable period has lapsed. Therefore, an assay based on antigen expressed by immature worms may serve to complement the existing procedures.

As a first step towards investigating the utility of the DiT33 molecule in early diagnosis of heartworm infection, a recombinant antigen-based antibody detection assay was developed and a panel of clinically defined sera was examined. Recombinant antigens can be generated in large quantities and have been used successfully to diagnose important filarial infections of humans including *O. volvulus* (Chandrashekar, et al., *J Clin Invest* ;88:1460–1466 (1991); Lobos, et al., *Mol Biochem Parasitol.,* 39:135–146 (1990); Lobos, et al., *Science* 251:1603–1605 (1991)) and *B. malayi* (Chandrashekar, et al., *Mol Biochem Parasitol.,* 64:261–271 (1994); Dissanayake, et al., *Mol Biochem Parasitol* 62:143–146 (1993)).

Antibody responses to DiT33 were observed in dogs during the pre-patent period and first appeared around the $L_4/L_5$ molt (11 weeks post infection). A transient delcine in response was observed in some animals at weeks 15 and 23 which may be due to the formation of immune complexes. At the onset of patency (27 weeks postinfection in this study), the antibody response to DiT33 was strong, yet as many as 50% of these sera scored negative in commercial antigen tests. Therefore, the commercial kits possess a low level of sensitivity for pre-patent and early patent infections. The inability to detect these infection, and infections with male worms only, (McCall, et al., Proc. Am. Assoc. Vet. Parasitol. 1993:36) is due to the fact that the target antigen is predominantly found in the uterus and eggs of female worms (Weil, et al., *J Immunol* 134:1185–1191 (1985)). The DiT33 antigen is expressed by both male and female worms, and in preliminary studies, antibody responses to DiT33 were detected in some dogs which received transplants of male worms (data not shown). Previous studies have shown that DiT33 is not expressed by infective larvae (Mejia, et al., supra) and in accordance with the present invention, it has been demonstrated that this antigen does not react with sera from dogs given chemical prophylaxis. Therefore, the DiT33 assay should distinguish established infections from successfully terminated early larval infections which are found in dogs given the commonly prescribed macrolides.

Historically antibody detection methods using crude antigen preparations have lacked the specificity associated with commercial antigen detection tests. However, in accordance with the present invention, it has been demonstrated that a high level of specificity (100%) can be achieved when a single, defined antigen is used. This supports the possibility of using an antibody detection test in heartworm diagnosis. Probably the most important advantage of antigen tests is their direct association with living worms which allows the veterinarian to distinguish past and current infections (Weil, et al., *Am. J. Trop. Med. Hyg.,* 33:425–430 (1984) and Weil, et al., *J. Immunol.,* 134:1185–1191 (1985), the disclosures of which are hereby incorporated by reference herein). However, antigenemia may persist for a considerable period and 12 weeks are required for the antigen used in commercial kits to decline to a satisfactory level following adulticide treatment for *D. immitis* (American Heartworm Society, *Proceedings of the American Heartworm Symposium* (1992), pages 289–294). Our observation that IgG responses to DiT33 decreased significantly between weeks 4 and 8 posttreatment may suggest the clearance of native DiT33 no less rapidly than the circulating antigens which the current commercial kits detect. Another important feature of antigen detection tests is the inclusion of an immune complex disassociation step which may provide greater sensitivity (Hamilton, *Am. J. Vet. Res.*, 45:2055–2061 (1984) and Weil, (1985) supra, the disclosures of which are hereby incorporated by reference herein). Described below in the Examples is an assay to detect circulating DiT33 antigen and/or immune complexes which may offer increased sensitivity in the early weeks of infection.

The general findings of this invention indicate that DiT33 is a promising antigen for the early detection of *D. immitis* infection and may be a valuable accessory in the management of heartworm disease.

As noted above, our initial work demonstrated the presence of a homolog of the *O. volvulus* antigen Ov33 in *D. immitis* (see Example I). DiT33 was initially purified using rabbit anti-MBP/OvD 5B antisera in immunoblots, a doublet of 31 and 33 kDa was observed in adult male, adult excretory/secretory components and microfilarial extracts of *D. immitis*. An additional band of 21 kDa present in adult worm material was recognized by anti-MBP/OvD 5B antibodies which probably represents a breakdown product of the 31–33 kDa molecule. These antibodies did not react with any antigens from infective larvae. Previous results indicate that *O. volvulus* parasites express the Ov33 molecule in a similar manner (Lucius et al., *Journal of Experimental Medicine*, supra (1988a)). DiT33 purified in this manner was found to be substantially free of other antigenic determinants from *D. immitis*.

Sera from chimpanzees experimentally infected with *O. volvulus*, were examined for reactivity with recombinant Ov33 and antibodies were detected around patency (Lucius et al., *Tropical Medicine And Hygiene*, supra (1992)). In accordance with the present invention, we show that sera collected from dogs experimentally infected with *D. immitis*, including animals with occult infection, were strongly reactive with the MBP/OvD 5B fusion polypeptide. In contrast to the chimpanzee data, the response to the Ov33 homolog in *D. immitis* as assayed with MBP/OvD 5B, was initially detected 11 weeks post-infection, coinciding with the L4/L5 molt in dogs. A relatively large number of dogs infected with *D. immitis* develop occult infections which have no circulating microfilariae. These animals obviously present a challenge for diagnosis yet 87% of occult animals tested in this study displayed a significant response to MBP/OvD 5B.

The ability to necropsy animals infected with *D. immitis* offers a unique opportunity to correlate antibody responses and worm burden. In cats which were experimentally infected with infective larvae or received transplants of adult worms, we were able to show a significant response to MBP/OvD 5B. We were also able to detect responses in cats naturally infected with *D. immitis*, despite the fact that these animals typically have low numbers of adult worms and few or no microfilariae.

Heartworm infection is largely controlled today by chemoprophylaxis. The infrequent occurrence of parasites in treated dogs is a result of the high efficacy of currently available drugs. However, brief lapses in drug administration or insufficient dosage may result in a mature infection with associated pathology. In accordance with the present invention, we demonstrate that animals treated with anthelminthic one month post infection did not respond to MBP/OvD 5B. This suggests as demonstrated in more detail below that we can distinguish dogs with adult worm infection from animals which have only been exposed to early larval forms.

Previous southern blotting experiments indicated that homologs of Ov33 may exist in *B. malayi* and *D. immitis* (Lucius et al., *Journal of Experimental Medicine*, supra (1988b)). The gene has recently been cloned in *B. malayi* (Bm33) (Dissanayake et al., *Molecular and Biochemical Parasitology*, supra (1993) and *Acanthocheilonema viteae* (Av33) (Willenbucher et al., *Molecular and Biochemical Parasitology*, supra (1993)). Interestingly, despite the sharing of antigenic determinants by members of this family of proteins. Ov33 has been shown to have potential in diagnosis of onchocerciasis. High levels of specificity can be achieved based on the detection of IgG4 responses to Ov33 (Lucius et al., *Tropical Medicine and Hygiene*, supra (1992)). We have demonstrated significant antigenic crossreactivity between the *O. volvulus* and *D. immitis* molecules. This relationship apparently does not extend to other parasites of cats and dogs, since a large number of sera collected from animals harboring various other helminth infections did not to react with the *O. volvulus* fusion protein.

In addition to the antigenic crossreactivity between Ov33 and DiT33 observed at the protein level, the similarities extend to their post-translational modifications. Jacalin, which is specific for the O-linked T antigen (a tumor cell marker) (Sastry et al., *Journal of Biological Chemistry*, 261:11726–11733 (1986)), was the only lectin found to bind DiT33 or Ov33. We have previously shown that jacalin binds to a large number of molecules in various stages of *D. immitis* (Mejia & Carlow, *Parasite Immunology*, 16:157–164 (1994)). Further characterization of DiT33 using O-glycanase revealed that the upper band of the doublet (33 kDa) was fully resistant, while the lower band (31 kDa) contained both resistant and susceptible moieties (data not shown). Lectin blot analysis of both Ov33 and DiT33 suggested an absence of N-linked glycans. This is consistent with our observation that PNGase F does not affect DiT33.

Our overall findings reveal a close relationship between the *O. volvulus* Ov33 and *D. immitis* DiT33 molecules. In addition, we have shown that responses to Ov33/DiT33 can be detected in pre-patent or occult cats and dogs. Therefore these antigens should be useful in diagnosis of heartworm infection and in the assessment of the experimental *D. immitis* infections in drug and vaccine trials.

In accordance with another embodiment of the present invention, the isolation and characterization of a complete cDNA encoding DiT33 has been provided. DiT33 was cloned as a fusion protein and expressed in *E. coli*. More specifically, DiT33 was cloned as a fusion protein with MBP and serological analysis performed using dog sera.

The DNA encoding the DiT33 or a fragment thereof, obtained from *D. immitis* can be used in the identification and isolation of related genes from other organisms, including other parasitic nematodes. For example, the DNA can be used in Southern blot to screen for related genes from other organisms.

One preferred method for the isolation and expression of this recombinant pepsin inhibitor is described in detail in the Examples. However, as the skilled artisan will appreciate once the sequence of DiT33 is known, a number of techniques familiar to the skilled artisan can be used to isolate DiT33 or DNA sequences corresponding to related genes. For example, a cDNA or expression library may be produced in a conventional manner by reverse transcription from messenger RNA (mRNA) from an organism found to possess the desired sequences, for example, by Southern blot analysis. To select clones containing DNA sequences encoding DiT33 or related proteins, hybridization probes corresponding to a portion of the *D. immitis* cDNA can be produced and used to identify clones containing such sequences. Preferred probes include a fragment from nucleotide 301 to nucleotide 648 of SEQ ID NO:3. Screening of the expression library with antibodies generated against the target DiT33 protein or Ov33/OvD 5B/Oc3.6, or a fragment thereof, may also be used. Genomic libraries may also be used. Such techniques are taught in Sambrook, Molecular Cloning, Second edition, Cold Spring Harbor Laboratory, Cold Spring Harbor Laboratory Press (1989)).

If desired, the DNA thus obtained can then be sub-cloned for further manipulation using techniques familiar to the skilled artisan. For example, the DNA can be subcloned into a vector such as pBR322 or pUC19.

Once identified, the DNA sequence coding for DiT33 or related proteins can be cloned into an appropriate vector such as a plasmid derived from *E. coli*, for example, pET3A, pBluescript or pUC19, the plasmids derived from the *Bacillus subtilis* such as pUB110, pTP5 and pC194, plasmids derived from yeast such as pSH19 and pSH15, bacteriophage such as λ phage, bacteria such as *Agrobacterium tumefaciens*, animal viruses such as retroviruses and insect viruses such as Baculovirus.

Overexpression of the target protein, in this case DiT33, can be achieved, for example, by separating the DNA encoding the target protein from its endogeneous control elements and then operably linking the DiT33 gene to a very tightly controlled promoter such as a T7 expression vector. See, Rosenberg, et al., *Gene*, 56:125–135 (1987). Insertion of the strong promoter may be accomplished by identifying convenient restriction targets near both ends of the DiT33 and compatible restriction targets on the vector near the promoter, and transferring the DiT33 gene into the vector in such an orientation as to be under transcriptional and translational control of the strong promoter.

DiT33 may also be overexpressed by utilizing a strong ribosome binding site placed upstream of the DiT33 gene to increase expression of the gene. See, Shine and Dalgamo, *Proc. Natl. Acad. Sci. USA*, 71:1342–1346 (1974).

The recombinant vector is introduced into the appropriate host using standard techniques for transformation and phage infection. For example, the calcium chloride method as described by Cohen, *Proc. Natl. Acad. Sci. USA*, 69:2110 (1972), is used for *E. coli*. The transformation of Bacillus is carried out according to the methods of Chang, et al., *Molecular and General Genetics*, 168:111 (1979). Transformation of yeast is carried out according to the method of Parent, et al., *Yeast*, 1:83–138 (1985). Certain plant cells can be transformed with *Agrobacterium tumefaciens*, according to the method described by Shaw, et al., *Gene*, 23:315 (1983). Transformation of animal cells is carried out according to, for example, the method described in *Virology*, 52:456 (1973). Transformation of insect cells with Baculovirus is carried out according to, for example, the method described in *Biotechnology*, 6:47 (1988).

The transformants are cultivated, depending on the host cell used, using standard techniques appropriate to such cells. For example, for cultivating *E. coli*, cells are grown in LB media at 30° C. to 42° C. to mid log or stationary phase.

DiT33 can be isolated and purified from a culture of transformed host cells, for example, by either extraction from cultured cells or the culture solution.

When the protein is to be extracted from a culture cell, the cells are collected are cultivation by methods known in the art, for example, centrifugation. Then, the collected cells are suspended in an appropriate buffer solution and disrupted by ultrasonic treatment, lysozyme and/or freeze-thawing. A crude extract containing the protein is obtained by centrifugation and/or filtration.

When DiT33 or related proteins are secreted into the culture solution, i.e., alone or as a fusion protein with a secreted protein such as maltose binding protein, the supernatant is separated from the cells by methods known in the art.

The separation and purification of DiT33 or related proteins are contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific affinity chromatography, methods utilizing difference in hydrophobicity such as reverse-phase high performance liquid chromatography and methods utilizing a difference in isoelectric point such as isoelectric focusing electrophoresis.

As noted above, DiT33 can be used as the basis for either an antibody-based or antigen-based assay for detecting the presence of heartworm in mammals, and in particular dogs and cats, as early as 11 weeks post-infection.

The antibody-based assay is described in more detail in Example I.

In general and in its broadest aspect, the antigen-based assay involves providing a sample of serum from a dog infected with or suspected of being infected with *Dirofilaria immitis* and analyzing the same for the presence of the circulating DiT33 antigen of *Dirofilaria immitis* by means of immunologic techniques using the monoclonal antibodies of the invention or polyclonal or polyvalent antibodies. Thus, the identification and characterization of circulating DiT33 described herein in accordance with the invention likewise renders possible detection by means of such assay techniques in order to diagnose hearworm in mammals, and in particular dogs and cats.

More specifically, the antigen-based assay may be carried out by combining a sample of blood or bodily fluid from an animal infected with or suspected of being infected with *Dirofilaria immitis* with a monoclonal antibody specific for DiT33, the monoclonal antibody being in either its native (unmodified) state or chemically modified state whereby the presence of such antigens can be readily determined. Where a monoclonal antibody is employed in modified form, it may be labeled for example with an enzyme which provides a detectible signal, with the presence of the circulating parasite antigens being detected by means of such signal. It will be understood that such monoclonal antibodies may be labeled with a wide variety of labels conventionally employed in counting and in diagnostic assays. Such labels may include, but are not limited to, radioactive labels, fluorescent compounds, enzymes, biotin, ferromagnetic labels or the like. In each instance, the binding of the monoclonal antibody to the binding sites or determinants present on the DiT33 found in the serum of *D. immitis* infected dogs or constituent epitopes thereof will provide for detection of and assaying for the presence of the antigens. In lieu of the monoclonal antibodies of the presence of the antigens. In lieu of the monoclonal antibodies of the invention but less advantageously, polyvalent or polyclonal antibodies may be utilized and be similarly labeled to provide a detectible signal in the convention manner.

The monoclonal antibodies of the invention may also be employed in unmodified or native form for carrying out assays for determining the presence of DiT33 by double antibody assay (e.g., sandwich ELISA assay) techniques known in the art. In such techniques, the monoclonals may be used as both the first and second antibodies or as the first antibody with a labeled polyclonal antibody being used as the second antibody or vice versa.

The present invention is further illustrated by the following Examples. These Examples are provided to aid in the understanding of the invention and are not construed as a limitation thereof.

The references cited above and below are herein incorporated by reference.

EXAMPLE I

Materials and Methods

Parasites

Adult worms, microfilariae and mosquitoes (*Aedes aegypti*) containing infective larvae of *D. immitis* were purchased from TRS Laboratories Inc. (Athens, Ga.). Infective larvae were collected from cold-anesthesized mosquitoes using a Baermann apparatus. Female worms of *O. volvulus* were dissected from nodules kindly provided by Prof. P. J. Ham, University of Keele, England.

Parasite Extracts 10 adult male worms of *D. immitis* were pulverized on dry ice and homogenized in 10 ml phosphate buffered saline (PBS) containing a cocktail of protease inhibitors (Boehringer Mannheim, Indianapolis, Ind.) comprising antipain dihydrochloride 50 µg/ml, APMSF 10 µg/ml, aprotinin 1 µg/ml, bestatin 4 µg/ml, chymostatin 10 µg/ml, E-64 5 µg/ml, EDTA 1 mM, leupeptin, 0.5 µg/ml, pepstatin 0.7 µg/ml and phosphoramidon 10 µg/ml. The homogenate was centrifuged (100,000×g, 1 h) to obtain a soluble fraction (PBS extract) and stored at −70° C.

Excretory/secretory (E/S) antigen of *D. immitis* was obtained from adult worms essentially as described (Poole et al., *Proceedings of the Academy of Science, USA*, 89:5986–5990 (1992) incorporation by reference is made herein). Worms were incubated in RPMI 1640 medium, 1% (wt/vol) glucose, penicillin 100 u/ml, streptomycin 100 µg/ml, and amphotericin 25 µg/ml (Gibco/BRL, Gaithersburg, Md.), at 37° C. and 5% $CO_2$. Spent media was pooled, filtered (0.22 µm) and concentrated using an ultrafiltration stirred cell containing an Mr 10,000-cutoff Diaflo membrane (Amicon, Beverly, Mass.).

A SDS extract of adult female worms of *O. volvulus* was prepared by homogenizing parasites in 1% SDS. The homogenate was processed as above.

Production Of MBP/OvD 5B

OvD 5B was cloned as described herein below. The original λgt11 phage was isolated from an *O. volvulus* adult worm cDNA library (Donelson et al., *Molecular and Biochemical Parasitology*, 31:241–250 (1988) incorporation by reference is made herein) by screening for *O. volvulus* specific antigens and then subcloned for over-expression in the Protein Fusion and Purification System in accordance with the manufacturer's instructions (New England Biolabs, Beverly, Mass.), with the following modifications. Cells were induced at mid log with 0.1–0.5 mM IPTG at 20° C. overnight. Fusion protein was prepared as described in the above Protein Fusion And Purification System in accordance with the manufacturer's instructions.

MBP/OvD 5B was purified on amylose resin as described by the manufacturer (New England Biolabs, Beverly, Mass.) and was further purified by passage over a FPLC MonoQ column (Pharmacia, Piscataway, N.J.).

Sera

Dog and cat sera were purchased from TRS Laboratories. For species-specificity studies, serum samples were collected from dogs harboring one or more of the following common parasites: *Toxocara canis*, *Toxascaris leonina*, *Ancylostoma caninum*, *Dipetalonema reconditum*, *Taenia* spp., or from cats with uncharacterized, intestinal helminth infection. Animals experimentally infected with *D. immitis* were known to lack intestinal helminths or infection with *D. reconditum* (dogs). Rabbit anti-MBP/OvD 5B antibodies were generated in New Zealand White rabbits following immunization with 100 µg MBP/OvD 5 B in Freunds' Complete Adjuvant (Sigma St. Louis, Mo.) given intramuscularly. The animals received a similar injection in Freunds' Incomplete Adjuvant after 2 (intramuscular) and 6 weeks (subcutaneous).

Affinity Purification Of Native Ov33 and DIT33 From *O. volvulus* and *D. immitis* Using Rabbit Anti-MBP/OvD 5B Rabbit anti-MBP/OvD 5B antibodies were bound to protein A-sepharose beads (Sigma, St. Louis, Mo.). 100 µl of beads was added to 1 ml of *D. immitis* male worm PBS extract (1.6 mg/ml), or 1 ml of a SDS extract of *O. volvulus* (diluted 1:10 with PBS containing 1% Triton X-100). After incubation for 1 h at room temperature the beads were washed 3 times with PBS 0.1% Triton X-100 (PBS-T). Immunopurified antigens were eluted with 200 µl of 0.1M glycine buffer pH 2.5, and the pH neutralized with 1M Tris pH 8.0.

Immunoblotting

MBP/OvD 5B (2 µg), intact infective larvae (180/lane), microfilariae (5000/lane), adult worm PBS extract (6.4 µg/lane) or E/S (3.2 µg/lane) or the immunopurified material (30 µg) were boiled for 5 min in SDS-PAGE sample cocktail (containing 3.2M urea, 1% SDS and 5% 2-mercaptoethanol final concentration). Samples were microfuged for 5 min and the supernatants were electrophoresed on 10–20% SDS-PAGE mini-gels (Diiachi, Tokyo, Japan) and transferred to nitrocellulose. Nitrocellulose membranes were stained with Ponceau S solution in 5% acetic acid (Sigma, St. Louis, Mo.), rinsed with distilled water, and blocked with 1% milk in PBS. The strips were incubated in rabbit (1:500) or dog (1:100) sera diluted in PBS-T containing 1% milk, followed by biotinylated sheep anti-rabbit IgG (H&L) antibody (Vector, Burlingame, Calif.) or biotinylated sheep anti-dog (H&L) antibody (Biodesign International, Kennebunkport, Me.) diluted 1:500 in PBS-T. Bound antibodies were detected using an avidin-biotin-peroxidase system (Vectastain ABC kit, Vector). The strips were washed with PBS-T and developed with 4-chloro-1-naphthol (Sigma, St. Louis, Mo.).

Enzyme-Linked Immunosorbant Assay (ELISA)

Wells of microtitre plates (Dynatech Laboratories, Chantilly, Va.) were coated overnight at 4° C. with an optimum concentration of MBP fusion protein (5 ng/well) in 0.05M carbonate buffer, pH 9.6. Following 2 washes in 0.05% (v/v) Tween 20 (PBS-Tween), plates were blocked for 30 min with 2% milk in PBS-Tween. Following sequential incubations in appropriately diluted (PBS-Tween) dog antibody, 1:500 dilution of biotinylated sheep anti-dog IgG (H&L) antibody (Biodesign International, Kennebunkport, Me.), bound antibodies were detected using an avidin-biotin-peroxidase system (Vectastain ABC kit, Vector) as above. Finally the enzyme substrate Orthophenylenediamine (Sigma, St. Louis, Mo.) was added and the absorbance at 495 nm was determined.

Since some cats possess anti-MBP antibodies, MBP reactivity was subtracted from the values obtained using the fusion protein. Wells were coated with 10 ng fusion protein or 4 ng MBP, which approximately equates with the amount of MBP present in the fusion protein (as determined using rabbit anti-MBP antibodies). Cat sera (1:100) and peroxidase conjugated anti-cat IgG antibody (Cappel, Durham, N.C.) diluted 1:2000 were then added. 3,3'5,5'-Tetramethylbenzidine (Kirkegaard & Perry, Gaithersburg, Md.) was used as substrate.

Lectin blotting

The extent of glycosylation of Ov33 and DiT33 was determined by lectin blot analysis. Biotinylated Concanavilin A (Con-A), Erythrina cristagalli lectin (ECL), Artpocarpus integrifolia (jacalin), peanut agglutinin (PNA), Phaseolus vulgaris erthroagglutinin (PHA-E), Ricinus communis agglutinin I ($RCA_{120}$), soybean agglutinin (SBA), Sophora japonica agglutinin (SJA), and wheat germ agglutinin (WGA) were purchased from Pierce (Rockford, Ill.). Biotinylated Lycopersicon esculentum (LEA) and Vicia villosa isolectin $B_4$ ($VvB_4$) were purchased from Sigma. After electrophoresis and transfer, nitrocellulose membranes containing O. volvulus or D. immitis antigens affinity purified with rabbit anti-MBP/OvD 5B were blocked with 1% BSA in PBS (PBS-BSA) for 1 h at room temperature. Each strip was then incubated with 3 ml of a biotinylated lectin (20 μg/ml in PBS-BSA), washed with PBS-T, and developed using the avidin-biotin-peroxidase system described above.

Results

Expression Of An Ov33 Homolog By Various Stages Of D. immitis

Figure 1:
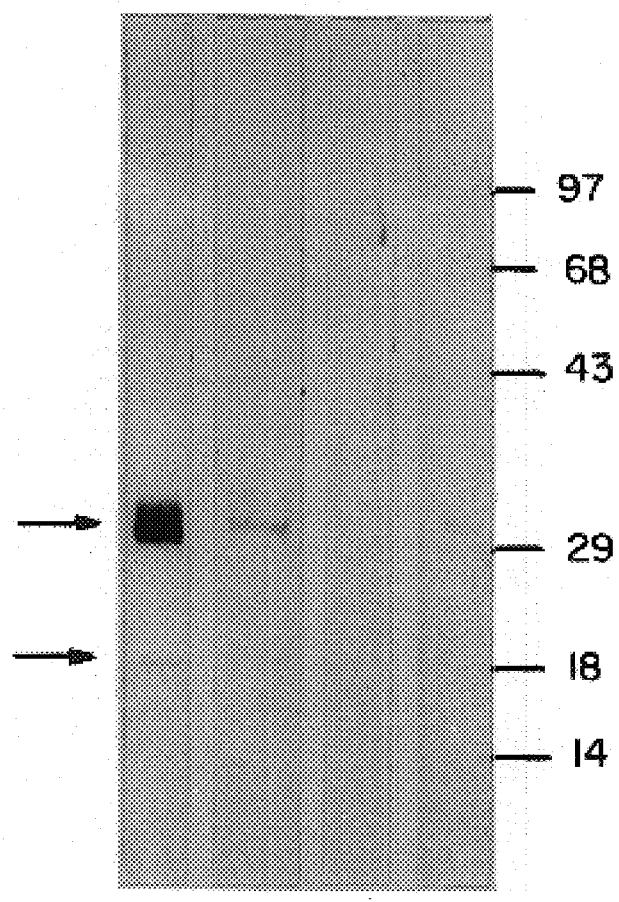
FIG. 1 illustrates the reactivity of rabbit anti-MBP/OvD 5B antisera with various stages of *D. immitis*. Adult male PBS extract (lane 1), adult male E/S antigen (lane 2), infective larvae (lane 3) and microfilariae (lane 4) were examined in immunoblots. The arrows indicate 31–33 and 21 kDa antigens.

Polyclonal rabbit sera generated against MBP/OvD 5B was found to react with a doublet of 31 and 33 kDa present in PBS extracts of adult male worms, male E/S and microfilarial extracts of D. immitis (FIG. 1). In addition, a minor component of approximately 21 kDa was also detected in both adult PBS extract and E/S preparations. Neither of these antigens were recognized by rabbit antibodies raised against MBP. Infective larvae did not possess any molecule reactive with rabbit anti-MBP/OvD 5B sera.

Figure 2:
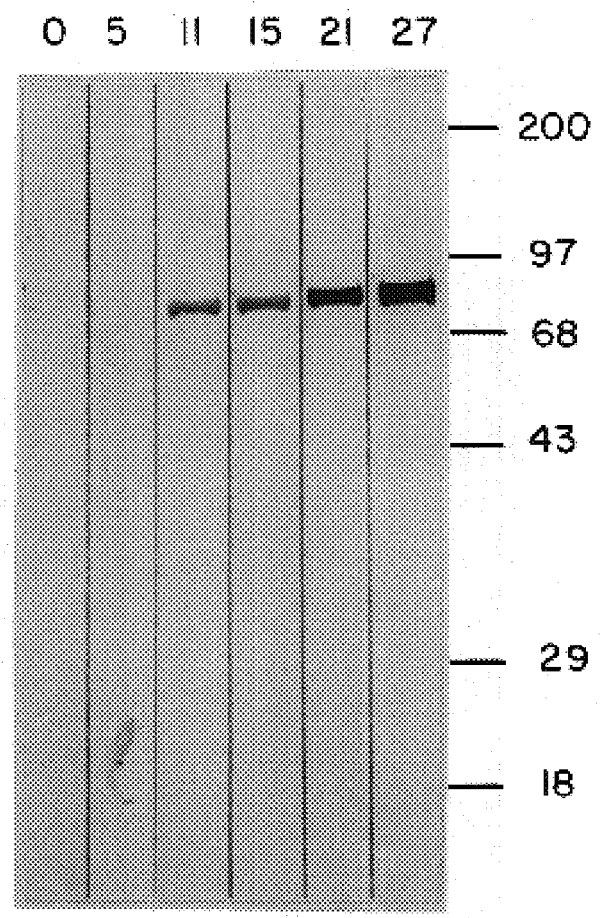
FIG. 2 illustrates the IgG response of dogs to MBP/OvD 5B during the course of infection with *D. immitis*. Sera were collected on weeks 0, 5, 11, 14, 21 and 27 p.i. from four dogs, pooled and examined in immunoblots.

Antibody Response Of Dogs To MBP/OvD 5B During The Course Of Infection With D. immitis To determine if the D. immitis homolog of Ov33 was antigenic, pooled sera from 4 dogs experimentally infected with D. immitis were examined for reactivity with MBP/OvD 5B on weeks 0, 5, 11, 15, 21 and 27 post-infection. An IgG response was initially detected in immunoblots 11 weeks post-infection which subsequently increased (FIG. 2). When the sera were examine individually by ELISA, a transient decrease in response was observed in 3 dogs around 15 weeks post-infection. The responses observed were directed against OvD 5B since these dogs did not possess anti-MBP antibodies. At week 27, when the animals were necropsied, comparable numbers (32–41) of adult worms were recovered from the hearts of all 4 dogs. Patency normally begins at approximately 6.5 months post infection with D. immitis. At necropsy, 2 of the 4 animals in this study were patent.

Antibody Response Of Dogs With Occult Heartworm Infection

Occult infection, in which dogs harbor a substantial number of adult worms without circulating microfilariae, occurs in a significant percentage of animals and is undetectable by current parasitological tests. The reactivity to MBP/OvD 5B in a group of 15 dogs with occult infection was analyzed. Antibodies were detected in 13 animals.

Antibody Response Of Dogs Following Heartworm Chemoprophylaxis

The antibody response to MBP/OvD 5B was examined in 16 dogs which received an infection comprising of 50 infective larvae of D. immitis. 4 weeks after infection all animals received 50 μg/kg ivermectin and serum was collected 4 months post infection. 6 months post infection, animals were necropsied and no adult worms were recovered. Of the 16 sera tested, only 1 was weakly reactive with MBP/OvD 5B.

Species-Specific Antibody Response Of Dogs To MBP/OvD 5B

Figure 3:
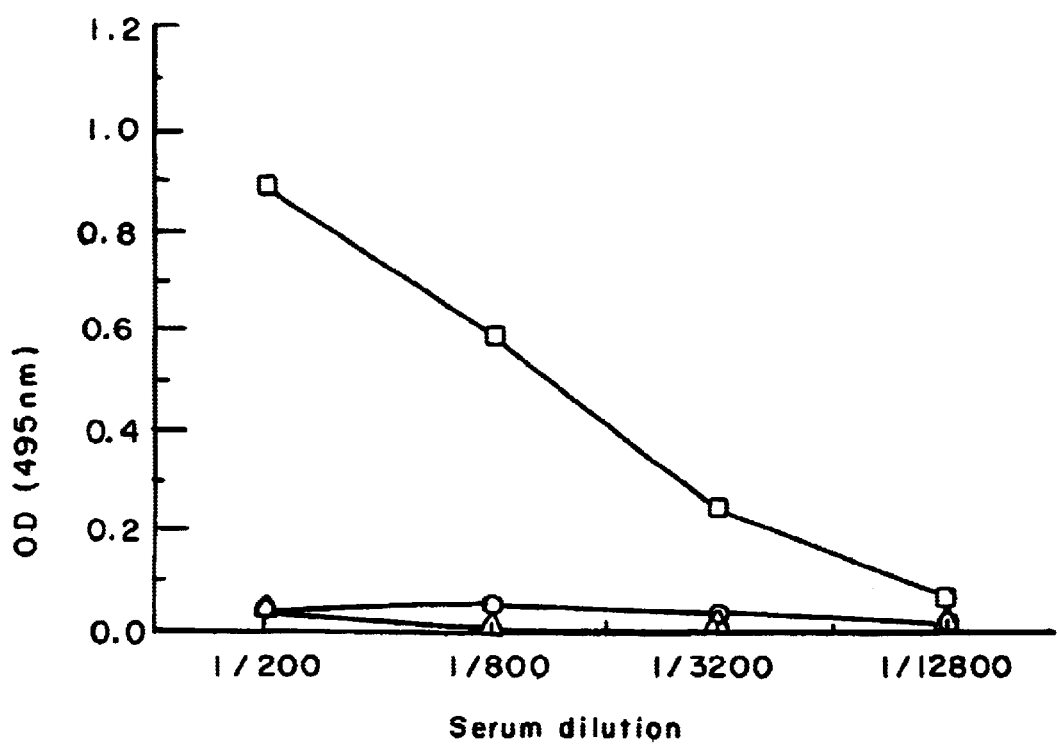
FIG. 3 illustrates the reactivity of sera from dogs harboring various helminth infections. The IgG response to MBP/

To determine if the responses observed in dogs were species-specific, 6 serum samples collected from animals harboring one or more of the following common parasites of dogs: Toxocara canis, Toxascaris leonina, Ancylostoma caninum, Dipetalonema reconditum, Taenia spp. were assayed for reactivity with MBP/OvD 5B. Sera collected from uninfected (negative) or D. immitis infected (positive) dogs were included as controls. Only the positive control sera reacted strongly with the recombinant antigen (FIG. 3). A total of 43 additional sera collected from dogs with other helminth infections were analysed in the same manner and none were found to react in this assay.

Antibody Response Of Cats Infected With D. immitis

Infection in cats is typified by the presence of few adult worms and a transient or absent microfilariaemia. In this study, 2 cats which were experimentally infected with 100 L3 larvae of D. immitis, possessed only 2 and 9 adult worms at necropsy and no microfilaraemia at weeks 24–28 post infection. These animals displayed a strong IgG response to MBP/OvD 5B (Table 1). Responses were detected earlier following transplant of 5–8 adult male and female worms. Comparable responses were obtained when sera were analyzed at 4–40 weeks post transplantation (Table 1).

TABLE 1

IgG response of D. immitis infected cats to MBP/OvD5B in ELISA*

| Months after infection[†] | | Months after adults worm transplantation[−] | | | |
|---|---|---|---|---|---|
| 6 | 7 | 1 | 2 | 3 | 10 |
| 1.000 | 1.060 | 0.650 | 0.760 | 0.780 | 1.020 |
|  |  | 0.970 | 0.700 | 1.130 |  |
|  |  | 1.010 | 0.980 | 0.970 |  |
|  |  |  | 0.640 | 0.970 |  |
|  |  |  |  | 0.720 |  |

*Each Value (O.D 495 nm) represents the response of a single cat
[†]Animals infected with 100L3 larvae of D. immitis
[−] Animals infected with 5–8 worms (both sexes) by injection in the jugular vein Sera from 13 cats obtained from animal shelters in the southern United States were examined for reactivity to MBP/OvD 5B. Of the 2 cats found to possess adult worms of *D. immitis*, a significant response was observed. The remaining 11 animals which possessed either intestinal helminths or no evidence of any helminthiasis did not react with the recombinant antigen.

Carbohydrate Analysis Of Ov33 and DIT33 Native Antigens

The native antigens of adult *O. volvulus* and *D. immitis* recognized by rabbit anti-MBP/OvD 5B sera were affinity purified and characterized further by lectin blot analysis. Several lectins were selected based on their differential carbohydrate-binding specificities: Con-A (mannose/glucose), jacalin (galactosyl(β-1,3)N-acetylgalactosamine), ECL (N-Acetyllactosamine), LEA (N-acetylglucosamine oligomers), PNA (galactosyl end groups), PHA-E (complex type sugars), SBA and RCA (N-acetylgalactosamine/galactose), SJA (β-D-N-acetylgalactosamine), $VvB_4$ (N-acetyl-D-galactosamine) and WGA (N-acetylglucosamine). Of all the lectins tested, only jacalin was found to react with the 31–33 kDa molecules of both *O. volvulus* and *D. immitis* (FIG. 4). In reciprocal experiments in which the 31–33 kDa molecules were affinity purified from *D. immitis* adult extract using jacalin, a strong reactivity with the rabbit anti-MBP/OvD 5B sera was observed.

EXAMPLE II

Cloning of OvD 5B

Female *O. volvulus* adult cDNA libraries (Donelson, et al (1988) *Molecular and Biochemical Parasitology* 31:241–250) were screened with sera generated against soluble female *O. volvulus* worm extract. Positive clones were plaque purified and screened for cross reactivity with *Ascaris lumbricoides* and *Loa loa* antigens. Clones which did not cross react with these sera were studied further. The inserts were subcloned into the maltose binding protein (MBP) expression systems (New England Biolabs, Inc., Beverly, Mass.) and the fragment ends were sequenced. OvD 5B was thus isolated.

Preparation of *O. volvulus*, *A. lumbricoides* and *L. loa* antigens and rabbit sera.

Each of these worm samples was frozen and ground in PBS pH 7 using a lead mortar and pestle. The mixture was refrozen and crushed again; the process was repeated 5 times at 1 hour intervals. The soluble extract was collected by centrifuging the mixture at 15000 RPM at 5° C. for 25 minutes and aspirating the supernatant. These supernatants (soluble antigens) were aliquoted and stored at −20° C. and were designated 'crude extract', 'worm extract' or simply 'extract' of the respective worms. The protein concentration of these extracts were determined by the method of Bradford (*Analytical Biochemistry*, 72:248–254 (1976)) (BioRad) using BSA as a standard.

New Zealand white rabbits were immunized separately with each of these extracts. The first dose was composed of 100 µg of antigen mixed with an equal volume of Freund's complete adjuvant. It was injected intramuscularly into the thighs of each rabbit. One week later, the second dose of the same amount of antigen, this time emulsified in Freund's Incomplete adjuvant was administered by the same route. The last boost was given one week later. It comprised the same amount of antigen dissolved in 0.1× PBS. The rabbits were bled from the main ear vein a week after the last antigen boost. After clotting for 2 hours at room temperature, the blood was stored overnight at 4° C. and then spun at 1500 RPM for 15 minutes. The serum was then aspirated and stored at −20° C. until needed. These sera will be referred to as anti-OV, anti-AL, and anti-LL sera.

The sera were preabsorbed on a column coupled to *E. coli* protein to remove antibodies to *E. coli* in order to reduce the background interference during the screening of the library. A culture of BNN97 cells (Young and Davis (1983) *Proc. Natl. Acad. Sci. USA.* 80:1194–1198) was grown in LB media to an OD reading at 600 nm of 0.5. They were then harvested and washed in coupling buffer (0.1 M Hepes pH 7, 80 mM $CaCl_2$). The cells were resuspended in coupling buffer to obtain a reading of $OD_{600nm}=1.00$, and thereafter sonicated on ice. The debris was spun down at 10,000 RPM and a Bradford protein determination was performed on soluble protein in the supernatant. Affi-gel 10 (BioRad Laboratories, Richmond, Calif.) resin was transferred to a 50 ml tube and pelleted at 1500 g at room temperature for 5 minutes. The resin was then washed 3 times in cold water and once in coupling buffer. The resin was mixed with the BNN97 soluble extract and the coupling reaction was allowed to proceed at room temperature for 4 hours. Excess BNN97 extract was removed by centrifugation at room temperature for 5 minutes at 1500 g and saved for determination of coupling efficiency. The resin was allowed to react with 1 column volume of 1 M Ethanolamine-HCl at room temperature for 1 hour. This was to block uncoupled sites on the resin. It was then washed in coupling buffer until the $OD_{280}$ of the wash was 0.2 and thereafter stored at 4° C. in coupling buffer to which has been added 0.1% sodium azide. Pre-absorption of anti-serum with the BNN97 immunosorbent column was undertaken using 1 to 5 ml anti-serum per ml of resin. The coupled resin was washed 2 times in TBS buffer (20 mM Tris 7.5–8, 150 mM NaCl), by resuspension and pelleting. The anti-serum, diluted ½ or ⅕ in TBS containing 1% BSA, 1 mM PMSF, was mixed with the resin and incubated overnight at 4° C. The mixture was subjected to constant shaking. The next morning, the resin was spun down at 1500 g for 1 minute at room temperature. The recovered antiserum was transferred into a clean tube. The final dilution was calculated and the clean antiserum aliquoted and stored at −20° C. or −70° C. prior to use in the screening.

Screening of an *O. volvulus* cDNA library with rabbit anti-*O. volvulus* sera.

The libraries were titered as follows (Sambrook et al, supra). *E. coli* strain ERI578 (New England Biolabs, Inc., Beverly, Mass.) was used as the plating stock. Serial dilutions of the library ($10^{-2}$, $10^{-3}$, $10^{-4}$, $10^{-5}$, $10^{-6}$, and $10^{-7}$) were made in SM buffer (Sambrook et al, supra). 200 µl of ERI578 cells ($OD_{600}=2$) was mixed with 3 ml melted top agar. This mixture was then poured onto pre-warmed LB ampicillin plates and left to solidify at room temperature for 5 minutes. 1 µl of each dilution of phage was spotted onto the plate and the phage were allowed to adsorb onto the cells at room temperature for 10 minutes followed by incubation overnight at 37° C. The next day the plaques were counted and the titer of the library was calculated.

Once titered, the cDNA library was screened with rabbit anti-OV sera (Young and Davis supra). Between 25,000 to 35,000 plaque forming units per plate were screened as follows. To 200 µl of ER 1578, was added the appropriate dilution of the recombinant phage in 10 ml glass tubes. The phage were adsorbed onto the cell surface for 15 minutes at room temperature without disturbing the mixture. 6 ml of melted top agar was added to the phage and immediately poured onto pre-warmed 15 cm wide LB ampicillin plates. The agar on the plates was left to solidify at room temperature for about 5 minutes. The plates were incubated at 42°

C. until plaques started to form (usually about 2 hours). S&S nitrocellulose filter circles previously wetted in 10 mM IPTG sterile solution were applied carefully under aseptic conditions onto the surface of the plate without forming air bubbles. The plate was incubated at 37° C. for 2 to 5 hours. The filter paper was marked not only to identify later which side was touching the surface of the plate but also to facilitate localizing the positive plaques. The filter paper was lifted carefully off the plate, washed with TBSTT (20 mM Tris 7.5–8, 150 mM NaCl, 0.% Tween 20, 0.05% Triton-X 100) before continuing the screening procedure using the western blotting technique. The filters were blocked for 1 hour in TBSTT with 3–5% non-fat dry milk. The filters were then washed 3 times in TBSTT, each wash lasting 5 minutes. The filters were incubated with a dilution of at least 1/100 of anti-OV sera in TBSTT for 1–2 hours at room temperature. After incubation with the primary antibody, the filters were washed 3 times with TBSTT, 5 minutes each time. Promega (Madison, Wis.) alkaline phosphatase conjugated anti-rabbit antibody was diluted to 1/7500 in 3% dry milk dissolved in TBSTT, and incubated with the nitrocellulose filters at room temperature for 30 minutes. After incubation with the secondary antibody, the filters were washed with TBSTT 3 times, 5 minutes each time. The reaction was developed with Promega (Madison, Wis.) NBT and BCIP for 0 to 60 minutes in the dark as per the manufacturer's instructions. The reaction was stopped with distilled water. The positive plaques were counted and identified on to the original plate from which they were recovered. The positive plaques were resuspended in SM buffer (Sambrook, et al supra) containing 1 drop of chloroform to kill the cells and stored at 4° C. as primaries in view of further screening. Positive phage were plaque purified as above.

During primary screening, about 500,000 plaques were screened, 347 clones reacted strongly with anti-OV sera, giving a probability of 7 positives per 10,000 phage. Of these positive plaques, 44 were selected randomly for further experimentation. These 44 phage were plaque purified 4 times to get 90 to 100% positives per small plate in order to ensure the homogeneity of each phage stock. Positive phage were tested for cross reactivity with anti-AL and anti-LL rabbit sera. Using a suitable dilution of each phage, 1 µl of phage was spotted onto an LB plate and incubated at 42° C. until plaques formed. IPTG wetted nitrocellulose filters were applied onto the surface of the plate and incubated for an additional 3 hours at 37° C. The filter was lifted off the plate and assayed using the anti-LL and anti-AL sera as described above for anti-OV sera primary screening. Phage reacting with anti-LL or anti-AL or anti-*Schistosoma mansoni* sera (human sera from infected travelers obtained as a gift from the Center for Disease Control, Atlanta, Ga.).

In order to generate stocks of the positive recombinant phage for further experiments, the plate wash method was used to prepare high titer phage lysates. 200 µl plating culture (ER 1578) was mixed with 25,000–50,000 phage. The mixture was incubated for 15 minutes at room temperature. 6 ml melted top agarose was added to this mixture and poured onto a 15 cm wide LB ampicillin plate which thereafter was incubated at 37° C. until growth of phage plaques was confluent. This generally takes about 5 to 7 hours. Plates were cooled at 4° C. for 30 minutes to harden the agarose and also to prevent infection of cells during harvesting. Plates were overlayed with 5 to 10 ml cold SM buffer per plate. Elution of the phage was carried out for 2 hours to overnight at 4° C., the plates shaken gently, when necessary. SM containing the phage was collected from each plate and separately pooled for each recombinant. The plates were again washed serially with 5 ml of SM which was recovered at the end of washing and added to the pool. About 4 drops of chloroform were added to the lysates and gently mixed to completely lyse any bacteria. The phage were titered and stored at 4° C. for future use.

Analysis of *O. volvulus* specific recombinants with emphasis on OvD 5B.

Phage which failed to cross react with the anti-LL and anti-AL sera were further analyzed for antigen expression. Transient lysogens were used to prepare very rapidly some recombinant protein with a view to sizing the proteins expressed by the clones. This facilitated selecting those that were fused to β-galactosidase. The essential steps were as follows. 1 ml of *E. coli* strain Y1089 (Young and Davis, supra), at an $OD_{600}$=2, was mixed with about $10^{10}$ phage in a 10 ml glass tube and the mixture was then incubated for 15 minutes at room temperature, without shaking. 6 ml of LB media were added to the phage/cells mixture. The infected cells were incubated at 42–45° C. with rapid shaking for 15 minutes. An IPTG solution was added to the culture to a final concentration of 5 mM. Ampicillin was added as well to give a concentration of 100 $\mu$g/ml. The culture was shaken constantly for an hour at 37° C. and the culture condition optimized to yield the best phage production with each recombinant clone. The cells were centrifuged in ependorf tubes (7000 RPM at room temperature for 2 minutes). The pellet was then freeze-thawed on dry ice to break up the cells. The urea lysis method was used to isolate recombinant antigen. The cell pellet was resuspended in urea lysis buffer (4 M urea, 2.5× SDS-PAGE sample buffer (Laemmli, U. K. (1979) *Nature* 227:680–685) to obtain 3% of the original culture volume. This mixture was passed several times through a 21 bore gauge needle to reduce the viscosity, or alternatively it was sonicated. The mixture was heated at 70° C. for 2 minutes and the insoluble material pelleted in an eppendorf tube (7000 RPM for 1 to 3 minutes at room temperature). The supernatant containing the recombinant protein was then stored at −20° C. for analysis. Western blot analysis (Towbin, *Proc. Natl. Acad. Sci. USA,* 76:4350–4354 (1979)) indicated that clone OvD 5B expressed an 145 kDa β-galactosidase fusion protein. ~114 kDa representing β-galactosidase sequences.

The sizes of the DNA inserts in the positive phage were analyzed by polymerase chain reaction (PCR) using opposing primers in λgt11. For 100 $\mu$l PCR reaction, the following were mixed: 1 $\mu$l of NEB primer 1222 (50–100 ng/$\mu$l), 1 $\mu$l of NEB primer 1218 (50–100 ng/$\mu$l), 10 $\mu$l of 10× Vent polymerase buffer (New England Biolabs, Inc. Beverly, Mass.), 5 $\mu$l of dNTP Mix (New England Biolabs, Inc., Beverly, Mass., 4 mM each), 79 $\mu$l of deionized water, 1 $\mu$l of phage lysate (see above), 2 $\mu$l of Vent DNA polymerase (New England Biolabs, Inc., Beverly, Mass.). This mixture was subjected to 20 amplification cycles (94° C. for 30 seconds for denaturation, 50° C. for 30 seconds for annealing and 72° C. for 2 minutes for extension) in a Perkin Elmer (Norwalk, Conn.) Thermocylcer 480. The products of the PCR were analyzed by 1% agarose gel electrophoresis. The fragment amplified from phage OvD 5B was approximately 1.1 kb.

Overexpression and purification of OvD 5B

The pMAL vectors provide a useful tool for expressing and purifying a protein expressed in *E. coli.* The cloned gene is inserted downstream from a malE gene, which encodes maltose-binding protein (MBP), and results in the expression of an MBP fusion protein. The method uses a strong tac promoter and malE translation initiation signals to give a high-level expression of the cloned sequences. It requires a one step purification for the fusion product using MBP's affinity for maltose. The pMAL C2 vector that was used lacks the signal sequence; the proteins expressed are therefore in the cytoplasm. This vector also contains the sequence coding for the recognition site of the specific protease, factor Xa. This allows MBP to be cleaved from the protein of interest after purification.

Since the λgt11 library was originally constructed by cloning cDNAs into the EcoRI site, and since OvD 5B produced a β-galactosidase fusion, then simple subcloning of the EcoRI fragment into a pMAL vector (New England Biolabs, Inc.,Beverly, Mass.) would result in an in frame fusion with the maltose binding protein (MBP) in the pMAL vectors. The pMAL C vector was digested with the restriction enzyme EcoRI. Both enzyme and vector were incubated for two hours at 37° C. in a 600 μl restriction digest composed as follows: 500 μl of vector (50 μg) DNA (New England Biolabs, Inc., Beverly, Mass.), 60 μl of 10× EcoRI buffer (New England Biolabs, Inc., Beverly, Mass.), 6 μl of 10 mM MgCl$_2$, 24 μl of deionized water (dH$_2$O), 10 μl of EcoRI (100 units, New England Biolabs, Inc., Beverly, Mass.). The vector was dephosphorylated to remove the phosphate group at the 5'-end of the vector in order to prevent reannealing of the vector ends resulting in circularization. The reaction was as follows. To the digested vector (49 μg) was added 4.9 μg of calf intestinal alkaline phosphatase. The reaction was allowed to proceed at 37° C. for 1 hour. 1 μg of digested and dephosphorylated vector (Cip'ed vector) was removed and saved for the ligation experiment.

The PCR amplified OvD 5B insert fragment was cleaned by phenol-chloroform extraction. To the DNA, an equal volume of phenol was added, mixed gently for 30 seconds and centrifuged for 5 minutes; the upper phase was recovered. After this, ½ volume of phenol and ½ volume of chloroform were added to the upper phase, vortexed for 30 seconds and then centrifuged for 5 minutes; again the upper phase was aspirated. The last extraction was done with 1 volume of chloroform as above. The upper phase was recovered and the DNA was ethanol precipitated at −20° C. overnight. After centrifugation, the pellet washed with 1 volume ethanol and air dried. The fragment was digested with EcoRI restriction enzyme as previously described for the vector. The digested fragment was isolated and purified by the low melting agarose method (Sambrook, et al supra), described below. The digested fragment was resolved by electrophoresis in a 1% low melt agarose gel (FMC Corp., Rockland, Me.). The gel was illuminated with a long wave UV lamp, the DNA band was excised with a clean razor blade and put into a clean eppendorf tube. This piece of agarose gel was melted at 45° C. in a water bath for 30 minutes and the DNA extracted by phenol-chloroform and precipitated with ethanol as above.

Ligation of the insert to the vector was tested at several molar ratios (1:1, 1:2, 1:4, vector:insert). Ligation mixtures contained 25 ng of CIP'ed vector, 2.5 μl of 10× ligation buffer (New England Biolabs, Inc., Beverly, Mass.) varying nanograms of insert according to the ratios chosen above, deionized water to 24 μl and 1 μl of T4 DNA ligase (New England Biolabs, Inc., Beverly, Mass., 4 units). The mixture was incubated at 16° C. overnight. For this reaction, the vector alone was ligated, to serve as positive control, and also to evaluate the background. 6 μl of each ligation reaction was used to transform TB1 competent cells (New England Biolabs, Inc., Beverly, Mass.). The transformation procedure is as follows. 12.5 ng of ligation sample was added to 200 μl competent cells and placed on ice for 30 minutes. This mixture was heat shocked at 42° C. for 90 seconds and then cooled on ice for 5 minutes. To it was added 800 μl LB medium, and then incubated for 45 minutes at 37° C. 100 μl of $10^{-1}$, $10^{-2}$ dilutions of the transformation mixtures were plated onto LB ampicillin plates previously spread with 80 μl of 2X-gal and 80 μl of IPTG. The plates were incubated overnight at 37° C. The next day the colonies were counted. Several methods were used to identify positive subclones. The initial method was color screening with plates containing IPTG and X-gal. Plasmids containing inserts would be white instead of blue. One would thus look for white colonies. White clones were tested for protein production as described in the New England Biolabs, Inc. Protein Fusion Manual (Riggs, *Current Protocols in Molecular Biology*, Supplement 19, Unit 16.6, pages 16.6.1–16.6.14). Briefly, 10 ml cultures of white colonies were induced with IPTG and lysates were examined after Coomassie Blue staining of SDS-PAGE gels. Colonies producing the correct size protein (expected size=~70–80 kDa with 42 kDa coming from MBP and ~30 kDa from the insert) were further characterized.

Next, 1 liter cultures were used to affinity purify the MBP-fusion protein on amylose resin (New England Biolabs, Inc., Beverly, Mass.). To 1 liter rich broth containing 100 mg/ml ampicillin was added 10 ml of an overnight culture of TB1 cells containing the OvD 5B plasmid. The cells were cultured to $2 \times 10^8$ cells/ml (OD$_{600}$~0.5) and induced with 3 mM IPTG. The induction was at 37° C. for 3 hours. The cells were harvested by centrifugation at 4000×g for 10 minutes at 4° C. and resuspended in 50 ml of lysis buffer (10 mM Na phosphate, pH 7.2, 30 mM NaCl, 10 mM β-mercaptoethanol, 1 mM EDTA). The cells were frozen to facilitate cell lysis or used immediately. Cells were then sonicated and lysis monitored by measuring the protein released by the method of Bradford (supra) until a maximum value was obtained. After complete sonication, cell debris was spun down and the supernatant collected. To prepare the affinity column, some pre-swollen amylose resin (New England Biolabs, Inc., Beverly, Mass.) was washed with 5 column volumes of amylose column buffer (10 mM Na phosphate, pH, 7.2, 0.5 M NaCl). The crude supernatant was diluted 5 times with column buffer and loaded onto the washed resin at a flow rate of 1 ml/minute at 4° C. The unbound proteins and the non-specifically weakly bound proteins were washed through the column with 10 column volumes of column buffer. Bound protein was eluted with 10 mM maltose in column buffer, and fractions of 3 ml were collected. These fractions were analyzed by the Bradford method for quantitation and SDS-PAGE for size and purity. Those fractions containing the MBP-OvD 5B fusion were pooled and frozen at −20° C. for further purification or for immediate use. In the case of OvD 5B, induction at 37° C. resulted in mostly cleaved MBP and little full length fusion. Different times and temperatures of induction were tested. For OvD 5B, the optimum temperature of induction is below 20° C. for 3 hours to overnight. Fast protein liquid chromatography (FPLC) on MonoQ columns (Pharmacia, Piscataway, N.J.) was used when necessary to separate the full length fusion from breakdown products.

Factor Xa cleavage to remove the MBP from the OvD 5portion of the fusion was attempted at several concentrations (0.5–2% w/w ratio), temperatures (room temperature or 4° C.) and times (1 hour to overnight).

Partial DNA sequencing of OvD 5B

The recombinant pMAL C plasmid encoding the MBP-OvD 5B fusion was partially sequenced (Sanger et al, *Proc.*

*Natl. Acad. Sci. USA,* 74:5463–5467 (1977)) using primers from within the vector sequence (NEB 1237 and NEB 1224). Sequence analysis of the end of the OvD 5B insert indicated that it encoded a member of the Ov33 family first described by Lucius et al., (1988) supra, called Ov33-3 and later by Chandrashekar et al., (1991) supra, called Oc 3.6. A close analysis revealed some differences at the 5'-end (FIG. 5) because our clone was larger than the previously described clones and because our sequence was preliminary data from a single sequencing run. The sequence obtained with NEB primer 1224 represents the 3'-end of the cDNA fragment and represents the antisense strand (ie., the reverse direction of translation). It is similar to the 3'-end of the Ov33-3 sequence, but continues past the end of Ov33-3. Despite being very preliminary sequence data, this information was sufficient to indicate that OvD 5B encoded an Ov33-like protein.

OvD 5B sequence (SEQ ID NO:10) with primer NEB 1224 (Note that this sequence includes the EcoRI site (GAATTC)):

```
  1 GAATTCCTTT TTAAAAAACG AGGATGTTTA TTACATTTTA AAAAAATTAA
 51 TTTCATAGAA GCAAACAGAC AGCTATGAAA AATAAAATGA TAATAAAAAG
101 TGATCAGGGT TAGCAAAACG AAGAGAAAAA TAGCTAAATT GATACAAAAA
151 TCAGCATTTA AAAGTAACTT
```

Plasmid DNA encoding the OvD 5B fusion vector has been deposited under the terms and conditions of the Budapest Treaty with the American Type Culture Collection.

EXAMPLE III

Isolation and Characterization of a DNA Encoding the DiT33 Antigen of *Dirofilaria Immitis*

Affinity Purification Of Dog Anti-OvD 5B/DIT33 Antibodies

Laboratory raised dogs were experimentally infected with *D. immitis* as described (Mejia & Carlow (1994) supra.

Antibodies reactive with MBP/OvD5B were purified on nitrocellulose from sera collected 27 weeks post infection with *D. immitis*. MBP/OvD5B (50 μg) was boiled for 5 min in SDS-PAGE sample cocktail (containing 3.2M urea, 1% SDS and 5% 2-mercaptoethanol final concentration). The sample was microfuged for 5 min and the supernatant was electrophoresed on 10–20% SDS-PAGE mini-gels (Diiachi, Tokyo, Japan) and transferred to nitrocellulose. Nitrocellulose membranes were stained with Ponceau S solution in 5% acetic acid (Sigma, St. Louis, Mo.), rinsed with distilled water, and the band corresponding to the fusion protein was then excised horizontally as a single strip. The strip was blocked with 1% milk in PBS and incubated in dog (1:100) sera diluted in PBS-T containing 1% milk for 1 h at 37° C. Following 3 washes with PBS 0.1% Triton X-100, the immunopurified antibodies were eluted with 0.1M glycine buffer pH 2.5, and the pH neutralized with 1M Tris pH 8.0.

Screening A *D. immitis* cDNA Library

All reagents, kits and bacterial strains used in cloning and expression (below) were obtained from New England Biolabs, Inc. (Beverly, Mass.) and used as described by the manufacturer, unless otherwise specified. A *D. immitis* adult worm cDNA library in λgt11 (Grandea et al., *Mol. Biochem. Parasitol.* 35:31–41 (1989)) was kindly provided by Dr. L. McReynolds (New England Biolabs, Inc., Beverly, Mass.) and approximately 100,000 phage were immunoscreened with affinity purified dog anti-MBP/OvD5B antibodies.

Sequencing

Positive clones were then subcloned into pUC19 for sequencing. The complete sequence of the cDNA encoding DiT33 was determined in both directions using the Circum-Vent Thermal Cycle Dideoxy DNA Sequencing Kit, or using an ABI 373A automated sequencer (Applied BioSystems Division, Perkin-Elmer Corporation, Foster City, Calif.) and Taq DyeDeoxy Terminator Cycle Sequencing Kit (Applied BioSystems Division, Perkin-Elmer Corporation, Foster City, Calif.).

DNA sequences were analyzed using the Genetics Computer Group (GCG) Software. The derived amino acid sequences were aligned using the program PILEUP (gap weight=3.0 gap length weight=0.1).

Nucleotide and Deduced Amino Acid Sequence of DIT33

Four of the 7 clones identified were similar to Ov33 by end terminal sequence analysis and 3 contained full length coding sequences for DiT33. The clone with the longest 5' untranslated sequence was completely sequenced in both directions. This cDNA (FIG. 6) is 785 bp long and contains 12 nucleotides of the nematode-specific 22 nucleotide spliced leader sequence (Takacs et al. *Proc. Natl. Acad. Sci.* 85:7932–7936 (1988)). The open reading frame encodes a 234 amino acid (aa) protein (26.4 kD) with a predicted pI of 8.1. A potential signal peptide is present (von Heijne, *Eur. J. Biochem.* 133:17–21 (1983)), suggesting a cleavage site after residue 17 (Alanine). The predicted amino acid sequence does not contain any potential N-linked glycosylation sites based on the absence of the consensus sequence NXS/T (Kornfield & Kornfield *Ann. Rev. Biochem.* 54:631–634 (1985)).

The deduced DiT33 amino acid sequence was compared to the known amino acid sequences of the pepsin inhibitor (Aspi3) from *Ascaris suum* and the deduced amino acid sequences of homologs from various filarial species (FIG. 7). The filarial proteins are considerably larger (233–235 amino acid) in size than the Ascaris protein (149 amino acid) due to 3 additional blocks of sequence (DiT33 residues 1–28, 82–112, 173–201). In common with other members of this family of proteins, the *D. immitis* sequence also possesses the conserved cysteine residues, and the entire YVRDLT (SEQ ID NO:11) motif which has been postulated to be the 'active site' of the pepsin inhibitor (Willenbucher et al. *Mol. Biochem. Parasitol.* 57:349–351 (1993)). The *D. immitis* sequence is more closely related (% identity/% similarity) to the Ov33 (83%/89%), Bm33 (76%/87%) and Av33 (75%/88%) sequences than to the Aspi3 (30%/49%) sequence.

EXAMPLE IV

Purification and Characterization of Recombinant DIT33

Subcloning Into pMALc2 And Expression of MBP Fusion Proteins

Primers were designed to enable cloning of DiT33 into the bacterial expression vector pMAL-c2 by polymerase chain reaction (PCR) to generate a fusion protein with MBP. The forward primer corresponded to the beginning of the open reading frame of DiT33 (minus a putative signal peptide, residues 1–17) and had the sequence 5'-AGCGTCATAAATCGACACAACAAACGT-3' (SEQ ID NO:12). The reverse primer corresponded to the last 6 residues of the protein, and included two termination codons and a Hind III recognition site (5'-CGCGAAGCTTCTATTAATAAATTGCAATACAGAA-3' (SEQ ID NO:13)). PCR was performed using Deep Vent DNA polymerase on 1 μg of template pUC19 DNA at 95° C./1 min., 50° C./1 min., 72° C./2 min. for 10 cycles followed by 72° C. for 5 min. The PCR product was run on a 1% low melt-point agarose gel, excised and digested for 30 min with 2 U of β-agarase (New England Biolabs, Inc., Beverly, Mass.). The supernatant was then phenol extracted and ethanol precipitated, and then resuspended in distilled water. Before ligation, the DNA was digested with XmnI and HindIII.

Ligation Into pMAL-c2 And Transformation

Ligation and transformation were essentially carried out as described in the New England Biolabs Protein Fusion and Purification System Instruction manual (New England Biolabs, Inc., Beverly, Mass.). Briefly, the pMAL-c2 vector was digested with XmnI and HindIII and a ligation of 1:28 vector to insert ratio was employed. The ligation was performed overnight at 16° C. with 4000 U T4 DNA ligase (New England Biolabs, Inc., Beverly, Mass.). The ligation mix was added to 50 μl of competant cells (ER 2267), and incubated on ice for 30 min, heated to 42° C. for 2 min, mixed with 900 μl of LB at 37° C. for 1 hour, and then plated out on LB/ampicillin plates and allowed to grow overnight.

Positive transformants were streaked onto an LB/ampicillin plate with 80 μg/ml X-GAL and 0.1M isopropyl β-D-thiogalacto-pyranoside (IPTG, Sigma, St. Louis, Mo.) for selection of white colonies. Miniprep DNA was prepared from the positive colonies using the Qiagen (Studio City, Calif.) miniprep system, following the manufacturers' recommendations.

Production And Purification Of MBP/DIT33

A single colony was picked and grown overnight at 37° C. in 20 ml of LB ampicillin and this was transferred to 2L of prewarmed rich broth plus ampicillin. The bacterial cells (strain ER2267) containing the DiT33-MBP fusion (NEB #1001) were grown at 37° C. to log phase (OD 600=0.8) and induced overnight at 12° C. with 0.5 mM IPTG. Following centrifugation at 5,000×g, the cells were resuspended in 200 ml column buffer (20 mM TrisHCl, 200 mM NaCl, 1 mM EDTA) and frozen overnight at −20° C. The suspension was thawed in cold water, sonicated for 1 minute each time until the suspension became clear. The sonicate was then centrifuged at 30,000×g and the supernatant was loaded onto a 2.5×15 cm amylose column which had been equilibrated with 10 volumes of column buffer. The column was washed with 8 volumes of regular column buffer and 2 volumes of column buffer containing 0.5M NaCl. MBP/DiT33 was eluted with column buffer plus 10 mM maltose. This procedure yielded 45–60 mg of fusion protein/L.

A sample of DiT33 in *E. coli* ER2267 (NEB#1001) has been deposited under the terms and conditions of the Budapest Treaty with the American Type Culture Collection on Mar. 29, 1996 and received ATCC Accession Number 98018.

EXAMPLE V

Serologic Analysis

Dog sera were purchased from TRS Laboratories Inc. (Athens, Ga.). All animals which were experimentally infected with *D. immitis* were laboratory raised and known to lack both intestinal helminths and *Dipetalonema reconditum* infection. For species-specificity studies, serum samples were collected from dogs harboring one or more of the following common parasites: *Toxocara canis, Toxascaris leonina, Ancylostoma caninum, Dipetalonema reconditum,* Taenia spp.

The enzyme-linked immunosorbent assay (ELISA) procedure used was as previously described (Mejia & Carlow, (1994), supra. All serum samples were tested in duplicate or triplicate. Wells of microtitration plates (Immulon® 2, Dynatech Laboratories, Chantilly, Va.) were coated with an optimum concentration of MBP/DiT33 (200 ng/100 μl/well) or MBP (80 ng/100 μl/well, as control) in 0.05M bicarbonate buffer, pH 9.6, at 4° C. overnight and then blocked with 2% milk in phosphate buffered saline (PBS) containing 0.05% (v/v) Tween 20 (PBS-Tw) at 4° C. overnight. Plates were dried by vacuum and sealed until use. After sequential 1 hour incubations at 37° C. in 100 μl of dog sera (diluted 1:100 or 1:200 in PBS-Tw) and biotinylated sheep anti-dog IgG (Biodesign International, Kennebunkport, Me.), diluted 1:500 in PBS-Tw, bound antibodies were detected using an avidin-biotin-peroxidase system (Vectastain® ABC kit, Vector, Burlingame, Calif.) and the substrate orthophenylenediamine (Sigma, St. Louis, Mo.). The color reaction was stopped with addition of 4 M $H_2SO_4$. Absorbance at 490 nm ($A_{490}$) was then determined. Before analysis absorbance values were corrected to a standard pool of sera from *D. immitis* infected dogs. A cut-off value was determined as the mean absorbance value plus three standard deviations of a pool of pre-infection sera.

DiroCHEK® (Synbiotics, San Diego, Calif.), Snap™ and PetChek® (IDEXX Laboratories, Westbrook, Me.) canine heartworm antigen test kits were purchased and used as directed.

Antibody Response Of Dogs To Recombinant DIT33 During The Course Of An Experimental Infection With *D. immitis*

Sera were collected from 4 dogs at routine intervals following an experimental heartworm infection. At week 27, when the animals were necropsied, comparable numbers of adult worms (31–41) were recovered from each dog, and 2 of the animals were microfilaremic.

FIG. 8A–FIG. 8D shows the IgG response of the dogs to MBP/DiT33 during the course of infection. A significant antibody response was observed in all dogs at week 11 post infection (p.i.) which then increased gradually and peaked at week 25 or 27 p.i. There was no significant difference in the responses of microfilaremic and non-microfilaremic dogs to MBP/DiT33. In control ELISA (MBP), dog sera did not react with MBP antigen. Therefore, the responses observed were directed to DiT33.

The same collection of sera were tested using the Diro-CHEK® and PetChek® kits and all samples collected prior to week 27 scored negative in both tests. Sera collected on week 27 were still negative when analyzed by DiroCHEK®, and were only borderline positive for 2 samples in PetChek® (Table 2, early patency). These 4 sera were also tested using Snap™. Only 1 sample yielded a borderline positive reading (Table 2, early patency)

TABLE 2

Results of DiT33 ELISA and Antigen Tests for Serodiagnosis of *D. immitis* Performed on Sera from Dogs with Necropsy Confirmed Infection Status

| Infection Status at Necropsy | Number of Samples Scored Positive | | | |
|---|---|---|---|---|
| | DiT33 ELISA | DiroCHEK® | PetChek® | Snap ™ |
| Early Patency (Week 27) | 4/4 | 0/4 | 2/4 | 1/4 |
| Patent | 4/4 | 4/4 | 4/4 | ND |
| Occutt | 14/15 | 12/15 | 13/15 | 11/15 |
| Di. reconditum* | 0/6 | 1/6 | 0/6 | ND |
| Other Helminths | 0/45 | 2/45 | 2/45 | ≧2/45# |
| Ivermectin Treated | 0/16 | 0/16 | 0/16 | ND |

All DiT33 ELISA tests were performed in duplicate with serum samples diluted 1:200. Commercial tests were scored blindly. False positive or false negative tests were repeated at least once and consistent results were obtained.
*Dipetalonema reconditum
ND = Not done
Only the 2 samples that were false positive by the other 2 antigen kits were tested.

Antibody Response Of Dogs With Occult Versus Patent Heartworm Infection

The antibody response to MBP/DiT33 was assessed in animals with immune-mediated occult (n=15) or patent (n=4) heartworm infection. As shown in Table 2, all animals, except one (occult) possessed antibodies reactive with MBP/DiT33. Both groups of serum samples produced similar $A_{490}$ values and ranges. On the other hand, the commercial antigen tests failed to detect 2–4 occult infections. The sample from an occult dog which scored negative in the DiT33 ELISA also scored negative by all 3 kits.

Based on the data (early patency, patent and occult samples) presented in Table 2, the overall sensitivity of the 4 assays was determined (Table 3). Sensitivity values of 96% (22/23), 70% (16/23), 83% (19/23) and 63% (12/19) were calculated for DiT33 ELISA, DiroCHEK®, PetChek® and Snap™ tests, respectively. However, the values for the commercial kits improved significantly (84%, 90% and 73%, respectively) if the early patency samples are excluded from the calculation.

TABLE 3

Sensitivity and Specificity of DiT33 ELISA and Commercially Available Assays Used in the Diagnosis of *D. immitis* Infection

| | DiT33 ELISA | DiroCHEK® | PetChek® | Snap ™ |
|---|---|---|---|---|
| Sensitivity % | 96 | 70 | 83 | 63 |
| Specificity % | 100 | 94 | 96 | ND |

Sensitivity = Number of infected dogs test positive/number of infected dogs tested. Specificity = Number of uninfected dogs test negative/number of uninfected dogs testes.

Species-Specific Antibody Response Of Dogs To DIT33

To determine if the responses observed in dogs were species-specific, a total of 51 serum samples collected from dogs infected with one or more of the following common parasites were assayed for reactivity to MBP/DiT33: *Dipetalonema reconditum, Taenia* spp., *Toxocara canis, Toxascaris leonina, Ancylostoma caninum* and *Trichuris* spp. These animals did not possess adult worms of *D. immitis* at necropsy. These sera were also processed using the standard antigen assays above and the results obtained from antibody and antigen assays were compared (Table 2).

As expected, the antigen assays possessed a high degree specificity, 94% and 96% for DiroCHEK® and PetChek®, respectively. The Snap™ test was not performed on all the samples from dogs with other infections and therefore a specificity value for this test was not determined. However, 100% specificity was observed in the DiT33 antibody test with the same samples (Table 3).

Antibody Response Of Dogs Given Prophylactic Treatment For *D. immitis*

The antibody response to MBP/DiT33 was examined in 16 dogs which were infected with 50 infective larvae of *D. immitis* and then given 50 µg/kg ivermectin 4 weeks later. Serum was collected from each animal 4 months p.i. At 6 months p.i, the animals were necropsied and no adult worms were found. None of the samples were reactive with DiT33 (Table 2). The same results were obtained using Diro-CHEK® and PetCheck® kits (Snap™ was not evaluated).

EXAMPLE VI

Circulating DIT33 Antigen Of *Dirofilaria immitis*, Polyclonal and Monoclonal Antibodies Specific Therefor and Methods of Preparing Such Antibodies and Detecting Such Antigen Production Of Polyclonal Anti-DIT33 Antibodies Rabbit anti-DiT33 antibodies were generated in a New Zealand White rabbit following immunization with polyacrylamide gel slices containing DiT33. Cleavage of MBP from the fusion protein was performed in 1 hour at 37° C. with 1% factor Xa protease, and the sample (550–750 µg) was boiled for 5 min in SDS-PAGE sample cocktail (containing 3.2M urea, 1% SDS and 5% 2-mercaptoethanol final concentration). The sample was microfuged for 5 min and the supernatant was electrophoresed on 10–20% SDS-PAGE mini-gels (Diiachi, Tokyo, Japan). The band corresponding to DiT33 was excised and pulverized. A total of 6 subcutaneous/intramuscular injections of 200–275 µg of DiT33 were administered in Freunds' Complete (first injection) and Incomplete Adjuvants (Sigma, St. Louis, Mo.) and injections were given 2–8 weeks apart. The polyclonal antibodies will bind to antigenic determinants on circulating DiT33 found in the serum of infected dogs.

Production Of Monoclonal Anti-DIT33 Antibodies

Monoclonal antibodies can be produced by hybridoma cell lines formed by fusion of cells from a mouse myeloma line and spleen cells (Carlow et al. *J. Parasitol.* 73:1054–1057 (1987)) from mice previously immunized with DiT33. An ELISA procedure as described above will be used to screen, select and clone the desired antibodies. The monoclonal antibodies will bind to antigenic determinants on circulating DiT33 found in the serum of infected dogs.

Mouse Immunization And Hybridoma Selection

Female mice (6–8 weeks old) of the BALB/c strain (The Jackson Laboratory, Bar Harbor, Me.) were immunized with polyacrylamide gel slices containing DiT33. Cleavage of MBP from the fusion protein was performed in 1 hour at 37° C. with 1% factor Xa protease, and the sample (55–82 µg) was boiled for 5 min in SDS-PAGE sample cocktail (containing 3.2M urea, 1% SDS and 5% 2-mercaptoethanol final concentration). The sample was microfuged for 5 min and the supernatant was electrophoresed on 10–20% SDS-PAGE mini-gels (Diiachi, Tokyo, Japan). The band corresponding to DiT33 was excised and pulverized. Animals received either 3 subcutaneous or intraperitoneal injections of 20–30 µg DiT33, in Freunds' complete (first injection) and Freunds' incomplete adjuvants.

The basic procedure for cell fusion will essentially be that of Fazekas de St. Groth and Scheidegger (*J. Immunol. Meth.* 35:1–21 (1980)). Hybridomas will be screened using a DiT33-based ELISA at least twice for antibody production, between days 10 and 14 after fusion. Cells from the positive wells will be cloned by limiting dilution within 5–10 days of screening, and recloned once thereafter.

Characterization Of Monoclonal Antibodies

Isotypes of antibodies produced in vitro by cloned cell lines will be determined by commercially available kits (Linscott Catalogue of Immunological Reagents (1996)). Antibodies for further characterization will be obtained following intraperitoneal injection of hybridoma cells into pristane-primed mice. Antigen specificity of monoclonal antibodies will be assessed by ELISA using DiT33 and antigen extracts prepared from other helminths. The epitope specificity of the monoclonal antibodies will be determined in inhibition studies (Nomura et al. *J. Immunol. Meth.* 58:1131 (1979)). Polyvinyl microtiter plates will be coated with DiT33 antigen as above. After blocking, the wells will be exposed to twofold dilutions of unlabeled monoclonal antibodies and incubated for 2 hours at 37° C. After washing, appropriately diluted biotinylated monoclonal antibodies will be added and the plate incubated for 1 hour at 37° C. The reaction will then be developed further as described in the DiT33 ELISA above.

Use Of Polyclonal Or Monoclonal Antibodies To Detect DIT33 In Sera From Infected Dogs Antigen capture assays will be performed using an ELISA format as described (Antibodies, A laboratory manual by Ed Harlow, David Lane. Cold Spring Harbor Laboratory publication (1988)). A variety of combinations of either polyclonal antibodies, monoclonal antibodies or both will be tested for antigen trapping and detection steps. The individual steps in the assay will be essentially as described above for the DiT33 ELISA antibody detection assay. Microtiter plates will be coated with polyclonal or monoclonal antibody. Varying amounts of antigen or dog sera, pre-treated to free antigen from immune complexes, will be added to the wells. Immune complexes will be isolated by adding an equal volume of 200 µl of 0.2M disodium EDTA (pH 7.5) and 100 µl of 12% polyethylene glycol (PEG 8000, Pharmacia, Piscataway, N.J.) in 0.1M borate buffer, pH 8.3. The mixture will then be incubated at 4° C. for 18 hours and then centrifuged at 15,000×g for 30 min. The precipitate will then be washed with cold 2.4% PEG in borate buffer. Several pre-treatment methods will be employed including dissolving the precipitates in PBS and boiling for 5 min, adding 0.1 M Tris/HCl, pH 2.6, or boiling in 0.1 M Tris/HCl, pH 2.6, followed by neutralization with 0.06 M $Na_2CO_3$ buffer, pH 9.6. After incubation and washing, appropriately diluted biotinylated antibody (100 µl) will be added. Detection of bound biotinylated antibody will be as described in the DiT33 ELISA.

What is claimed is:

1. An isolated and purified canine or feline *D. immitis* filarial parasite protein characterized by antigenic cross reactivity with a human *O. volvulus* (Ov33) filarial parasite protein and immune-reactivity with sera from cats or dogs having an early or late stage heartworm infection, the immune-reactivity having diagnostic sensitivity and specificity for detecting heartworm infection by 11 weeks post infection, wherein the glycosylated form of the *D. immitis* filarial parasite protein has a molecular weight of 31–33 Kd as determined by reducing SDS acrylamide gel electrophoresis.

2. A protein according to claim 1, wherein the purified protein is a product of a purification procedure comprising an antibody affinity column.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAATTCCGAA TAATTCCATC AAGAACAACA ACAATGAAAA TTCTTTTCGG TTGTTATTGC      60

TCGCATAACA GCATTGGAAG CAGGTGTTAG TAAAAAGGTA CAATAAACGT TTTGCTGGAT     120

TTAATGTTGC CGGAATTGGT GGAATGCTGG ATGTGTCGTT GTGGGATTTT AATAACTGTT     180
```

(2) INFORMATION FOR SEQ ID NO:2:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
CAAGAACAAC AACAATGAAA ATTCTTTTCT GTTTGTTATT GCTCGCGATA ACAGCATTGG      60

AAGCAGGTGT AGTAAAAAGG TACAATAAAC GTTTTGCTGG ATTTAATGTT GCCGGAATTG     120
```

```
GTGGAAATGC TGGATGTGTC GTTGTGGATA ATAAACTGTT                              160
```

(2) INFORMATION FOR SEQ ID NO:3:

(i) SEQUENCE CHARACTERISTICS:
        (A) LENGTH: 785 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 61..762

(xi) SEQUENCE DESCRIPTION: SEQ ID NO:3:

```
CCCAAGTTTG AGAATTACTT GGATTATACA AAATCGAGAA TATTTCAACA AAATAAAACT       60

ATG AAA ATT CTT TTC TGT TTC GTA TTG CTT GCG ATA GCA GCA TTG CGA        108
Met Lys Ile Leu Phe Cys Phe Val Leu Leu Ala Ile Ala Ala Leu Arg
 1               5                  10                  15

GCA AGC GTC ATA AAT CGA CAC AAC AAA CGT TTT GCC GGA TTC AGT GTT        156
Ala Ser Val Ile Asn Arg His Asn Lys Arg Phe Ala Gly Phe Ser Val
                 20                  25                  30

GCT GGA ATT GGT GGA ACT GCC GGA TGT GTT GTT GTT GAT AAT AAA CTT        204
Ala Gly Ile Gly Gly Thr Ala Gly Cys Val Val Val Asp Asn Lys Leu
             35                  40                  45

TTT GCG AAC AGC TTC TAT CTT CGT GAT CTA ACA ACC GAA GAG CAA AGA        252
Phe Ala Asn Ser Phe Tyr Leu Arg Asp Leu Thr Thr Glu Glu Gln Arg
 50                  55                  60

GAA CTT GCA CAA TAT GTT GAA GAT TCA AAT CAA TAC AAA GAA GAA GTA        300
Glu Leu Ala Gln Tyr Val Glu Asp Ser Asn Gln Tyr Lys Glu Glu Val
 65                  70                  75                  80

AAG ACA TCA TTG GAA GAA AGA CGT AAA GGA TGG CAA TTA GCA CGA CAT        348
Lys Thr Ser Leu Glu Glu Arg Arg Lys Gly Trp Gln Leu Ala Arg His
                 85                  90                  95

GGT GAG AAG GAT GCT AAA GTT TTA TCA TCA TTA GCA GAA AAG AAA TTC        396
Gly Glu Lys Asp Ala Lys Val Leu Ser Ser Leu Ala Glu Lys Lys Phe
            100                 105                 110

CCA AAA CCA CCA AAA AAA CCA TCA TTC TGC TCA GCT GGT GAT ACG ACA        444
Pro Lys Pro Pro Lys Lys Pro Ser Phe Cys Ser Ala Gly Asp Thr Thr
        115                 120                 125

CAA TAC TAT TTT GAT GGT TGT ATG GTT CAG AAT AAT AAA ATA TAT GTG        492
Gln Tyr Tyr Phe Asp Gly Cys Met Val Gln Asn Asn Lys Ile Tyr Val
    130                 135                 140

GGA CGA ATG TAT GTA CGT GAT TTA ACA TCC GAT GAA ATA AAT CAA CTG        540
Gly Arg Met Tyr Val Arg Asp Leu Thr Ser Asp Glu Ile Asn Gln Leu
145                 150                 155                 160

AAA ACA TTT GAT GCT AAA ATG ACA GCA TAT CAG AAA TAT TTG TCA TCG        588
Lys Thr Phe Asp Ala Lys Met Thr Ala Tyr Gln Lys Tyr Leu Ser Ser
                165                 170                 175

TCC ATT CAA CAG CAA GTT GAT AGC TTA TTT GGT GAT AAA TCA AAT CTA        636
Ser Ile Gln Gln Gln Val Asp Ser Leu Phe Gly Asp Lys Ser Asn Leu
            180                 185                 190

TTC AAT TTA TTC ACT GAT ACA CGT CAT GAA ACA TCA TCA CAA CCA TCC        684
Phe Asn Leu Phe Thr Asp Thr Arg His Glu Thr Ser Ser Gln Pro Ser
        195                 200                 205

GAT GCT ACA ACA ATC TCG ACA ACA ACT CAA GCT CCA GTT GAA CCA CCC        732
Asp Ala Thr Thr Ile Ser Thr Thr Thr Gln Ala Pro Val Glu Pro Pro
    210                 215                 220

GAA ACA CCA CAT TTC TGT ATT GCA ATT TAT TAAACAAAAA AAAAAAAAA           782
Glu Thr Pro His Phe Cys Ile Ala Ile Tyr
```

```
Glu Thr Pro His Phe Cys Ile Ala Ile Tyr
225                 230

AAG                                                                              785
```

(2) INFORMATION FOR SEQ ID NO:4:

(i) SEQUENCE CHARACTERISTICS:
        (A) LENGTH: 234 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Ile Leu Phe Cys Phe Val Leu Leu Ala Ile Ala Ala Leu Arg
1               5                   10                  15

Ala Ser Val Ile Asn Arg His Asn Lys Arg Phe Ala Gly Phe Ser Val
            20                  25                  30

Ala Gly Ile Gly Gly Thr Ala Gly Cys Val Val Asp Asn Lys Leu
        35                  40                  45

Phe Ala Asn Ser Phe Tyr Leu Arg Asp Leu Thr Thr Glu Glu Gln Arg
50                  55                  60

Glu Leu Ala Gln Tyr Val Glu Asp Ser Asn Gln Tyr Lys Glu Val
65                  70                  75                  80

Lys Thr Ser Leu Glu Glu Arg Arg Lys Gly Trp Gln Leu Ala Arg His
                85                  90                  95

Gly Glu Lys Asp Ala Lys Val Leu Ser Ser Leu Ala Glu Lys Lys Phe
            100                 105                 110

Pro Lys Pro Pro Lys Lys Pro Ser Phe Cys Ser Ala Gly Asp Thr Thr
            115                 120                 125

Gln Tyr Tyr Phe Asp Gly Cys Met Val Gln Asn Asn Lys Ile Tyr Val
    130                 135                 140

Gly Arg Met Tyr Val Arg Asp Leu Thr Ser Asp Glu Ile Asn Gln Leu
145                 150                 155                 160

Lys Thr Phe Asp Ala Lys Met Thr Ala Tyr Gln Lys Tyr Leu Ser Ser
                165                 170                 175

Ser Ile Gln Gln Gln Val Asp Ser Leu Phe Gly Asp Lys Ser Asn Leu
            180                 185                 190

Phe Asn Leu Phe Thr Asp Thr Arg His Glu Thr Ser Ser Gln Pro Ser
        195                 200                 205

Asp Ala Thr Thr Ile Ser Thr Thr Thr Gln Ala Pro Val Glu Pro Pro
    210                 215                 220

Glu Thr Pro His Phe Cys Ile Ala Ile Tyr
225                 230
```

(2) INFORMATION FOR SEQ ID NO:5:

(i) SEQUENCE CHARACTERISTICS:
        (A) LENGTH: 234 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:5:

```
Met Lys Ile Leu Phe Cys Phe Val Leu Leu Ala Ile Ala Ala Leu Arg
1               5                   10                  15

Ala Ser Val Ile Asn Arg His Asn Lys Arg Phe Ala Gly Phe Ser Val
```

```
            20                  25                  30
Ala Gly Ile Gly Gly Thr Ala Gly Cys Val Val Asp Asn Lys Leu
            35                  40                  45

Phe Ala Asn Ser Phe Tyr Leu Arg Asp Leu Thr Thr Glu Glu Gln Arg
50                  55                  60

Glu Leu Ala Gln Tyr Val Glu Asp Ser Asn Gln Tyr Lys Glu Glu Val
65                  70                  75                  80

Lys Thr Ser Leu Glu Glu Arg Arg Lys Gly Trp Gln Leu Ala Arg His
                    85                  90                  95

Gly Glu Lys Asp Ala Lys Val Leu Ser Ser Leu Ala Glu Lys Lys Phe
                100                 105                 110

Pro Lys Pro Pro Lys Lys Pro Ser Phe Cys Ser Ala Gly Asp Thr Thr
                115                 120                 125

Gln Tyr Tyr Phe Asp Gly Cys Met Val Gln Asn Asn Lys Ile Tyr Val
                130                 135                 140

Gly Arg Met Tyr Val Arg Asp Leu Thr Ser Asp Glu Ile Asn Gln Leu
145                 150                 155                 160

Lys Thr Phe Asp Ala Lys Met Thr Ala Tyr Gln Lys Tyr Leu Ser Ser
                165                 170                 175

Ser Ile Gln Gln Gln Val Asp Ser Leu Phe Gly Asp Lys Ser Asn Leu
                180                 185                 190

Phe Asn Leu Phe Thr Asp Thr Arg His Glu Thr Ser Ser Gln Pro Ser
                195                 200                 205

Asp Ala Thr Thr Ile Ser Thr Thr Thr Gln Ala Pro Val Glu Pro Pro
                210                 215                 220

Glu Thr Pro His Phe Cys Ile Ala Ile Tyr
225                 230

(2) INFORMATION FOR SEQ ID NO:6:

(i) SEQUENCE CHARACTERISTICS:
        (A) LENGTH: 235 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

Met Lys Ile Leu Phe Cys Leu Leu Leu Ala Ile Thr Ala Leu Glu
1               5                   10                  15

Ala Gly Val Val Lys Arg Tyr Asn Lys Arg Phe Ala Gly Phe Asn Val
            20                  25                  30

Ala Gly Ile Gly Gly Asn Ala Gly Cys Val Val Asp Asn Lys Leu
            35                  40                  45

Phe Ala Asn Ser Phe Phe Leu Arg Glu Leu Thr Thr Glu Glu Gln Arg
50                  55                  60

Glu Leu Ala Gln Tyr Ile Glu Asp Ser Asn Arg Tyr Lys Glu Glu Val
65                  70                  75                  80

Lys Glu Ser Leu Glu Glu Arg Arg Lys Gly Trp Gln Leu Ala Arg Asp
                85                  90                  95

Gly Lys Glu Asp Ser Lys Val Leu Ser Ala Leu Ala Glu Lys Lys Leu
                100                 105                 110

Pro Lys Pro Pro Lys Lys Pro Ser Phe Cys Ser Ala Gly Asp Thr Thr
                115                 120                 125

Gln Tyr Tyr Phe Asp Gly Cys Met Val Gln Asn Asp Lys Ile Tyr Val
```

```
                130                 135                 140
Gly Arg Ala Tyr Val Arg Asp Leu Thr Pro Asp Glu Val Thr Gln Leu
145                 150                 155                 160

Lys Thr Phe Asp Ala Lys Met Thr Ala Tyr Gln Lys Tyr Leu Ser Ser
                165                 170                 175

Thr Ile Gln Lys Gln Val Asp Ser Leu Phe Gly Lys Ser Asn Leu
                180                 185                 190

Phe Asn Leu Phe Ala Asp Thr Arg Thr Glu Ala Thr Ser Gln Ala Ser
                195                 200                 205

Asp Asp Ala Thr Ala Gly Ala Thr Thr Thr Gln Ala Pro Val Glu Ala
210                 215                 220

Pro Glu Pro Pro His Phe Cys Val Ala Ile Tyr
225                 230                 235

(2) INFORMATION FOR SEQ ID NO:7:

(i) SEQUENCE CHARACTERISTICS:
        (A) LENGTH: 234 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:7:

Met Lys Ile Leu Ser Cys Leu Leu Cys Thr Ile Thr Val Leu Glu
1               5                   10                  15

Gly Asn Val Met Asn Arg His Asn Lys Arg Phe Ala Gly Phe Asn Val
                20                  25                  30

Ala Gly Ile Gly Gly Thr Ala Gly Cys Val Val Asp Asn Lys Leu
                35                  40                  45

Phe Ala Asn Gly Phe Phe Leu Arg Glu Leu Thr Ala Glu Glu Gln Arg
50                  55                  60

Glu Phe Ala Gln Tyr Val Glu Glu Ser Asn Lys Tyr Lys Glu Glu Leu
65                  70                  75                  80

Lys Val Ser Leu Glu Glu Arg Arg Lys Gly Trp Gln Ile Ala Arg Gln
                85                  90                  95

Ser Lys Glu Gly Ala Lys Ile Leu Ser Thr Ile Thr Glu Lys Asn Leu
                100                 105                 110

Pro Lys Pro Pro Lys Lys Pro Ser Phe Cys Thr Ala Ala Asp Thr Thr
                115                 120                 125

Gln Tyr Tyr Phe Asp Gly Cys Met Val Gln Asn Asn Lys Ile Phe Val
                130                 135                 140

Gly Gln Ser Tyr Val Arg Asp Leu Thr Ala Asp Glu Ala Lys Glu Leu
145                 150                 155                 160

Lys Ser Phe Asp Val Lys Met Thr Ala Tyr Gln Lys Tyr Leu Ser Ser
                165                 170                 175

Ser Ile Gln Gln Gln Met Asn Ser Leu Phe Gly Asp Lys Thr Asn Leu
                180                 185                 190

Leu Asn Leu Phe Thr Asn Thr His Leu Glu Ser Thr Ser Gln Ala Ser
                195                 200                 205

Glu Ala Thr Thr Ile Pro Thr Thr Thr Gln Thr Pro Val Glu Ala Pro
210                 215                 220

Glu Thr Pro Ser Phe Cys Val Pro Ile Tyr
225                 230
```

-continued (2) INFORMATION FOR SEQ ID NO:8:

(i) SEQUENCE CHARACTERISTICS:
        (A) LENGTH: 233 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:8:

```
Met Lys Thr Leu Phe Cys Leu Leu Leu Phe Ala Ile Ala Val Leu Glu
 1               5                  10                  15

Ala Gly Ile Val Lys Arg Tyr Asn Lys Arg Phe Ala Gly Phe Asn Val
            20                  25                  30

Ala Gly Ile Gly Gly Thr Ala Gly Cys Val Val Asp Asn Lys Leu
        35                  40                  45

Phe Ala Tyr Gly Leu Pro Leu Arg Glu Leu Thr Ala Glu Glu Gln Lys
    50                  55                  60

Glu Leu Ser Arg Tyr Val Gln Glu Ser Asn Lys Tyr Lys Glu Asp Leu
65                  70                  75                  80

Met Thr Ser Leu Glu Glu Arg Arg Lys Gly Trp Gln Leu Ala Arg His
                85                  90                  95

Ser Lys Glu Gly Ser Lys Ile Leu Ser Ser Leu Ala Glu Lys Asn Phe
            100                 105                 110

Pro Lys Pro Pro Lys Lys Pro Ser Phe Cys Thr Ala Ala Asp Thr Thr
        115                 120                 125

Gln Tyr Tyr Phe Asp Gly Cys Met Val Gln Asn Asn Lys Ile Tyr Val
    130                 135                 140

Gly Arg Thr Leu Val Arg Asp Leu Ile Pro Glu Glu Val Lys Glu Leu
145                 150                 155                 160

Lys Thr Phe Asp Ala Lys Met Thr Ala Tyr Gln Lys Tyr Leu Ser Ser
                165                 170                 175

Ser Ile Gln Gln Gln Met Asp Asn Leu Phe Gly Asp Lys Thr Asn Leu
            180                 185                 190

Phe Ser Leu Phe Thr Glu Thr Tyr Leu Glu Thr Ser Pro Gln Thr Gly
        195                 200                 205

Glu Ala Thr Val Ser Thr Thr Thr Gln Val Pro Val Glu Ala Pro Glu
    210                 215                 220

Thr Pro Ser Phe Cys Ile Ala Ile Tyr
225                 230
```

(2) INFORMATION FOR SEQ ID NO:9:

(i) SEQUENCE CHARACTERISTICS:
        (A) LENGTH: 149 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:9:

```
Gln Phe Leu Phe Ser Met Ser Thr Gly Pro Phe Ile Cys Thr Val Lys
 1               5                  10                  15

Asp Asn Gln Val Phe Val Ala Asn Leu Pro Trp Thr Met Leu Glu Gly
            20                  25                  30

Asp Asp Ile Gln Val Gly Lys Glu Phe Ala Ala Arg Val Glu Asp Cys
        35                  40                  45
```

```
Thr Asn Val Lys His Asp Met Ala Pro Thr Cys Thr Lys Pro Pro Pro
     50                  55                  60

Phe Cys Gly Pro Gln Asp Met Lys Met Phe Asn Phe Val Gly Cys Ser
 65              70                  75                  80

Val Leu Gly Asn Lys Leu Phe Ile Asp Gln Lys Tyr Val Arg Asp Leu
                 85                  90                  95

Thr Ala Lys Asp His Ala Glu Val Gln Thr Phe Arg Glu Lys Ile Ala
            100                 105                 110

Ala Phe Glu Glu Gln Gln Glu Asn Gln Pro Pro Ser Ser Gly Met Pro
        115                 120                 125

His Gly Ala Val Pro Ala Gly Gly Leu Ser Pro Pro Pro Pro Pro Ser
    130                 135                 140

Phe Cys Thr Val Gln
145
```

(2) INFORMATION FOR SEQ ID NO:10:

(i) SEQUENCE CHARACTERISTICS:
        (A) LENGTH: 170 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:10:

```
GAATTCCTTT TTAAAAAACG AGGATGTTTA TTACATTTTA AAAAAATTAA TTTCATAGAA      60

GCAAACAGAC AGCTATGAAA AATAAAATGA TAATAAAAAG TGATCAGGGT TAGCAAAACG     120

AAGAGAAAAA TAGCTAAATT GATACAAAAA TCAGCATTTA AAAGTAACTT                170
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:11:

```
Tyr Val Arg Asp Leu Thr
 1               5
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
AGCGTCATAA ATCGACACAA CAAACGT                                          27
```

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown -continued (ii) MOLECULE TYPE: cDNA (xi) SEQUENCE DESCRIPTION: SEQ ID NO:13:

CGCGAAGCTT CTATTAATAA ATTGCAATAC AGAA  34